United States Patent
Litwak

(10) Patent No.: US 11,364,038 B1
(45) Date of Patent: *Jun. 21, 2022

(54) BLADES FOR OSTEOTOME

(71) Applicant: Palix Medical LLC, Keyport, NJ (US)

(72) Inventor: Alfred Anthony Litwak, Keyport, NJ (US)

(73) Assignee: Palix Medical LLC, Keyport, NJ (US)

( * ) Notice: Subject to any disclaimer, the term of this patent is extended or adjusted under 35 U.S.C. 154(b) by 276 days.

This patent is subject to a terminal disclaimer.

(21) Appl. No.: 16/826,392

(22) Filed: Mar. 23, 2020

Related U.S. Application Data

(63) Continuation-in-part of application No. 15/369,839, filed on Dec. 5, 2016, now Pat. No. 10,595,879.

(51) Int. Cl.
*A61B 17/16* (2006.01)
*A61B 90/00* (2016.01)

(52) U.S. Cl.
CPC .......... *A61B 17/1604* (2013.01); *A61B 90/05* (2016.02)

(58) Field of Classification Search
CPC ... A61B 17/16; A61B 17/1604; A61B 17/162; A61B 17/1626; A61B 17/1628; A61B 17/1633; A61B 17/1635; A61B 17/164; A61B 17/1642; A61B 17/1655; A61B 17/1657; A61B 17/1659; A61B 17/1662–1693; A61B 17/1695
USPC .......................................................... 606/84
See application file for complete search history.

(56) References Cited

U.S. PATENT DOCUMENTS

| | | | | |
|---|---|---|---|---|
| 4,150,675 A | * | 4/1979 | Comparetto | A61B 17/1604 30/316 |
| 4,600,005 A | * | 7/1986 | Hendel | A61B 17/1604 30/167 |
| 5,147,364 A | * | 9/1992 | Comparetto | A61B 17/15 606/85 |
| D342,313 S | * | 12/1993 | Hood | D24/146 |
| D344,801 S | * | 3/1994 | Hughes | D24/146 |
| 5,735,855 A | * | 4/1998 | Bradley | A61B 17/1604 606/86 R |
| 6,110,175 A | * | 8/2000 | Scholl | A61B 17/1604 606/79 |
| 6,187,012 B1 | * | 2/2001 | Masini | A61F 2/4607 606/99 |
| 6,485,495 B1 | * | 11/2002 | Jenkinson | A61B 17/32 606/167 |
| 6,790,211 B1 | * | 9/2004 | McPherson | A61F 2/4607 606/169 |
| 8,372,077 B2 | * | 2/2013 | Taylor | A61F 2/4607 606/82 |

(Continued)

*Primary Examiner* — Eric S Gibson
(74) *Attorney, Agent, or Firm* — Peter Materna

(57) ABSTRACT

Embodiments of the invention comprise a blade that has a gripping portion, a transition portion and a distal portion that may have a cutting edge. The gripping portion may be V-shaped in cross-section, or, more generally, not lying in a single plane. Some embodiments are straight along a longitudinal direction. Embodiments may comprise a transition portion that is complex having sub-regions, or a distal portion having a cross-sectional shape that is curved or V-shaped, or a distal portion having a tip of a different material. Other embodiments have a shape that follows a longitudinal path that is curved either concavely or convexly or both. Distal tip design parameters for good cutting properties are discussed.

19 Claims, 16 Drawing Sheets

(56) References Cited

U.S. PATENT DOCUMENTS

| | | | | |
|---|---|---|---|---|
| 8,545,501 | B2 * | 10/2013 | Wong | A61B 17/56 |
| | | | | 606/86 R |
| 8,734,450 | B2 * | 5/2014 | Landon | A61B 17/142 |
| | | | | 30/337 |
| 8,858,559 | B2 * | 10/2014 | Milburn | A61B 17/14 |
| | | | | 606/177 |
| 8,888,783 | B2 * | 11/2014 | Young | A61B 17/16 |
| | | | | 606/177 |
| 8,920,424 | B2 * | 12/2014 | Boykin | B27B 5/32 |
| | | | | 606/82 |
| 9,198,776 | B2 * | 12/2015 | Young | A61F 2/4607 |
| 9,848,900 | B2 * | 12/2017 | Witt | A61B 17/320068 |
| 9,867,628 | B2 * | 1/2018 | Macke | A61B 17/1742 |
| 10,595,879 | B1 * | 3/2020 | Litwak | A61B 17/142 |
| 2004/0098000 | A1 * | 5/2004 | Kleinwaechter | B23D 61/123 |
| | | | | D24/146 |
| 2007/0123893 | A1 * | 5/2007 | O' Donoghue | A61B 17/142 |
| | | | | 606/82 |
| 2011/0034932 | A1 * | 2/2011 | Paulos | A61B 17/16 |
| | | | | 606/84 |
| 2011/0288555 | A1 * | 11/2011 | Szanto | A61B 17/1637 |
| | | | | 606/84 |
| 2014/0316415 | A1 * | 10/2014 | Young | A61B 17/1637 |
| | | | | 606/84 |

* cited by examiner

Figure 1F
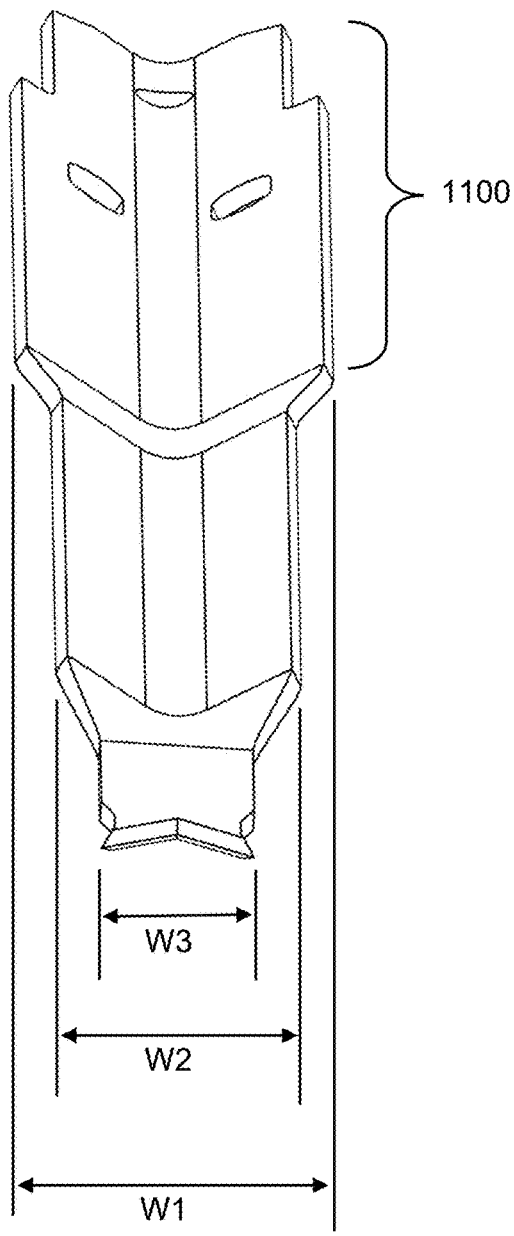
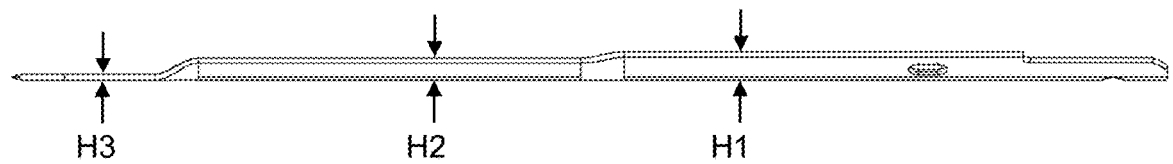
Figure 1G

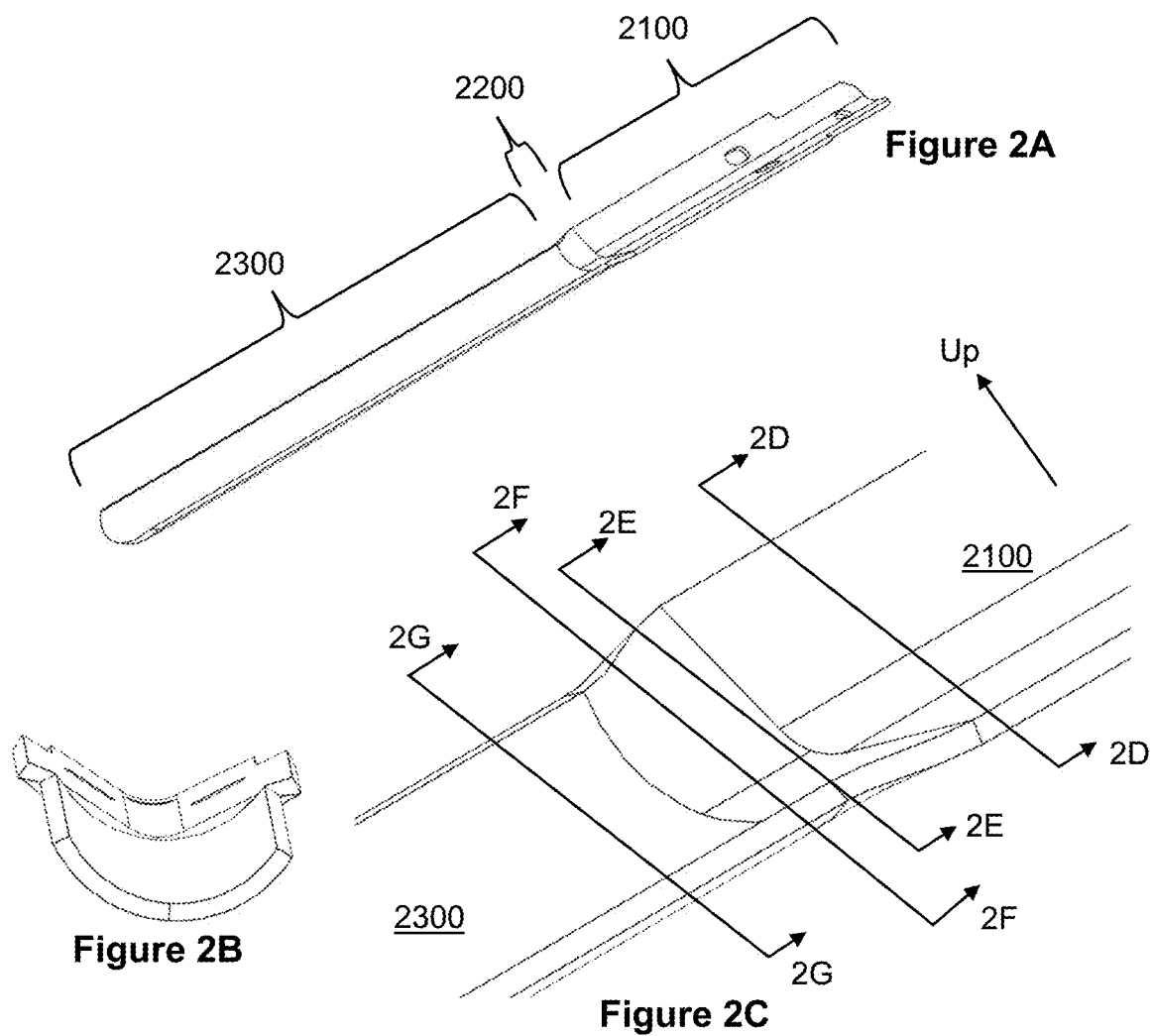
Figure 2A
Figure 2B
Figure 2C
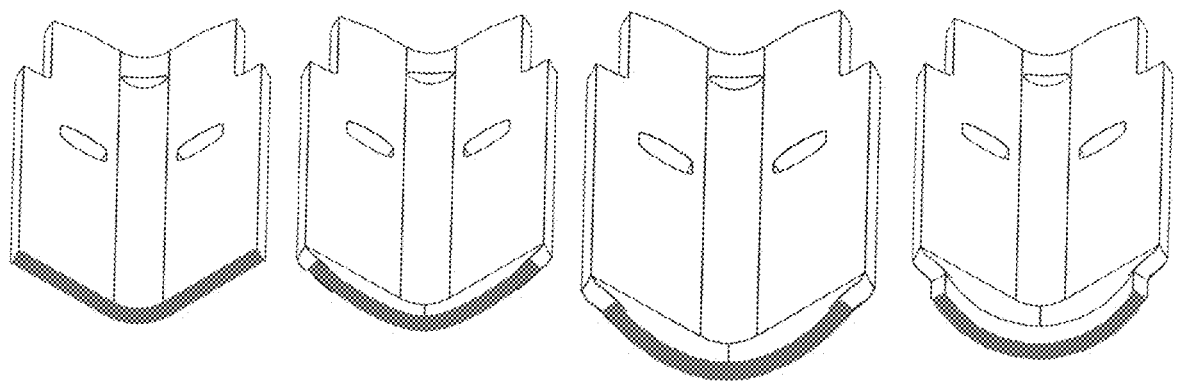
Figure 2D   Figure 2E   Figure 2F   Figure 2G

2300

2320

Rtip

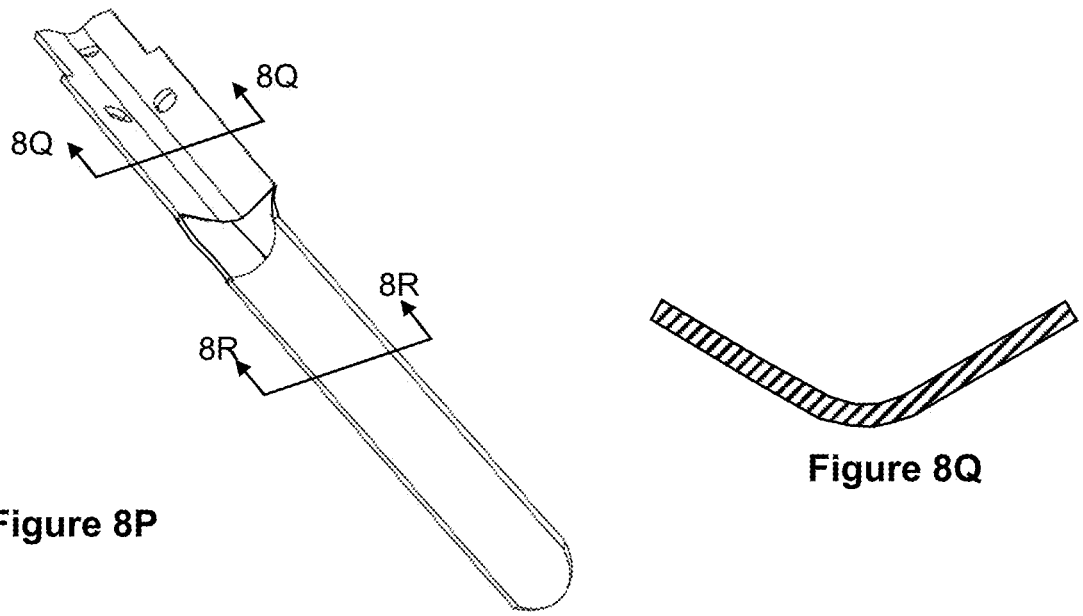
Figure 8P
Figure 8Q
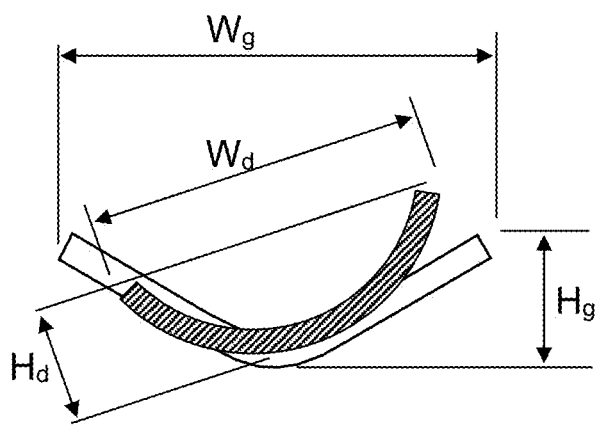
Figure 8R

BLADES FOR OSTEOTOME

CROSS-REFERENCE TO RELATED APPLICATION

This patent application is a Continuation-in-Part patent application of U.S. Ser. No. 15/369,839, now issued as U.S. Pat. No. 10,595,879, which is incorporated herein by reference in its entirety.

FIELD OF THE INVENTION

Embodiments of the invention pertain to cutting tools and orthopedic surgery.

BACKGROUND OF THE INVENTION

Orthopedic surgery frequently requires the use of blades or tools to cut bone, separate implants from bone, cut bone cement, or separate implants from bone cement. Such tools may be pneumatically driven, electrically driven, or hand operated. The blades or tools may have both a cutting portion that contacts the bone and a gripping portion that interacts with the powered device. The driving device typically applies to the blade/tool mechanical loads that are geometrically compressive along the length of the blade and that, as a function of time, are time-varying and often in the nature of an impact. The geometry of both the cutting portion of the blade and the gripping portion of the blade and the corresponding geometry of the driving device can influence the performance of the blade in terms of stiffness, ability to transmit force efficiently, and ability to access hard-to-reach anatomical spaces. Although a variety of such blades/tools exist, there still remains a need for improvement as far as surgeon convenience, ease of access to a surgical site, and load-transferring properties of the blade.

SUMMARY OF THE INVENTION

An embodiment of the invention may include a blade comprising: a gripping portion; a transition portion that is continuous with the gripping portion; and a distal portion that is continuous with the transition portion, wherein the gripping portion has a longitudinal axis and has a gripping portion cross-sectional shape taken perpendicular to the longitudinal axis, wherein the gripping portion has a gripping portion major surface that does not entirely lie in a single plane, wherein the distal portion has a distal portion cross-sectional shape that is different from the gripping portion cross-sectional shape, wherein the transition portion has a three-dimensional surface transitioning between the gripping portion and the distal portion.

Embodiments of the invention may have a gripping portion that has a cross-section that is V-shaped (with a vertex that is either pointed or rounded); may have a distal portion having a cross-section that is curved or V-shaped (with a vertex that is either pointed or rounded); may be straight along a longitudinal direction, or may follow a path that is non-straight; may have any of various geometries of cutting edge at the distal end; and may have a transition portion that is simple or more complex.

BRIEF DESCRIPTION OF THE ILLUSTRATIONS

Embodiments of the invention are further described but are in no way limited by the following illustrations.

FIG. 1A is a three-dimensional view of a generic blade that is straight in the longitudinal direction, having a distal portion that is flat. FIG. 1B is a three-dimensional view of a blade that is straight in the longitudinal direction, in which the transition portion comprises three sub-regions and the distal portion is flat. FIG. 1C is a cross-sectional view of the transition portion of the blade of FIG. 1B. FIG. 1D is a cross-sectional view of an alternate cross-sectional shape of the transition portion. FIG. 1E is a cross-sectional view of yet another alternate design in which the gripping portion is separated into two legs that are separate from each other. FIG. 1F is a view somewhat from above illustrating various width dimensions. FIG. 1G is a side view illustrating various height dimensions.

FIG. 2A is a three-dimensional view of a blade that is straight in the longitudinal direction, in which the distal portion has a cross-sectional shape that is curved. FIG. 2B is a view from a slightly angled perspective that is almost an end view. FIG. 2C is a close-up of a portion of FIG. 2A. FIGS. 2D, 2E, 2F and 2G are various cross-sections of the blade of FIG. 2A, taken either near or in the transition portion. FIG. 2H is a view from an angled perspective, somewhat a view from above, showing various width dimensions. FIG. 2I is a side view showing various height dimensions.

Figure 6A:
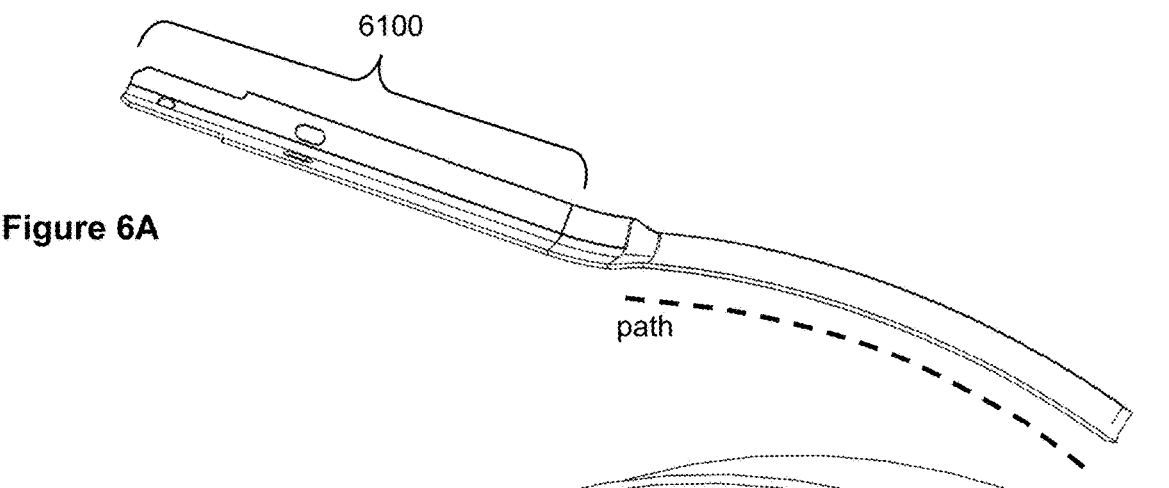
Figure 6B:
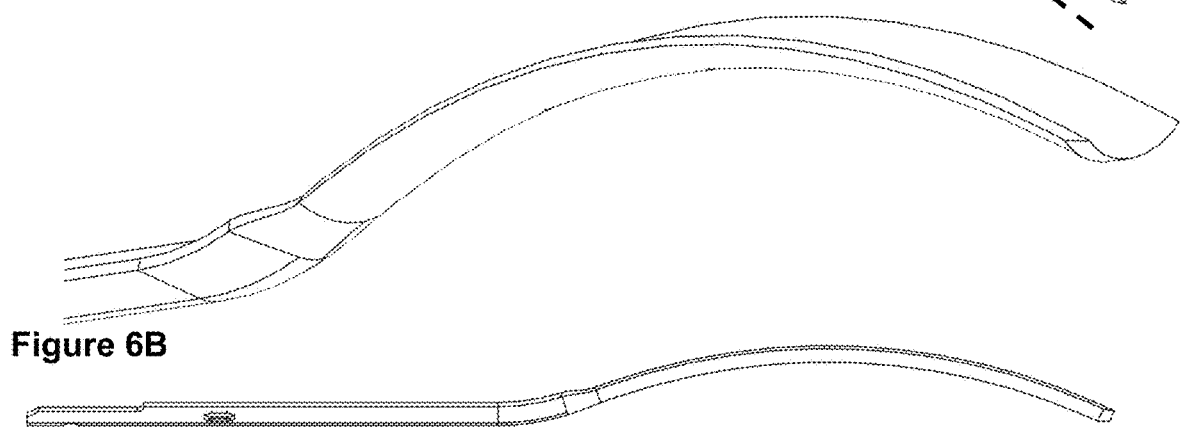
Figure 6C:
Figure 6D:

FIG. 6A is a is a three-dimensional view of a blade that is not straight but rather follows a path that is curved convexly. FIG. 6B is another three-dimensional view of the blade from a different perspective. FIG. 6C is a side view. FIG. 6D is a top view.

Figure 7:
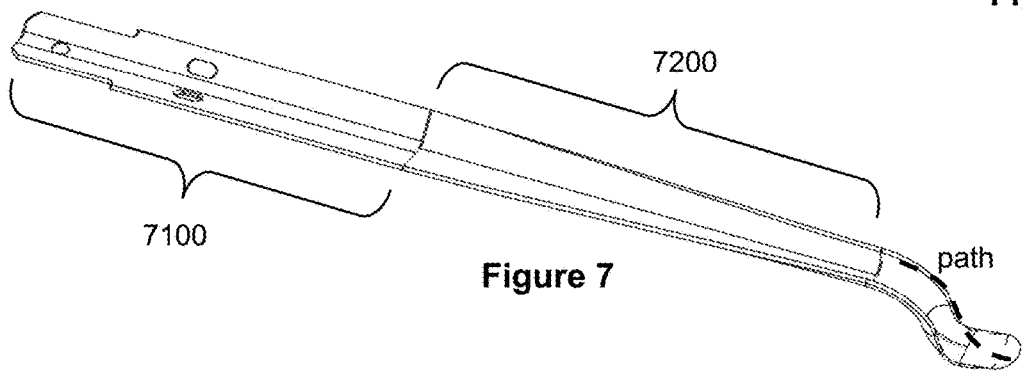

FIG. 7 is a three-dimensional view of a blade that is not straight but rather follows a path that is curved convexly in one place and concavely in another place.

FIGS. 8A-8F are views of geometries of the cutting edges of various blades in which the distal portion is flat or planar. FIGS. 8G and 8H are three-dimensional perspective views of an advantageous cutting blade, shown together with a splash guard. FIG. 8I is a side view of the same blade. FIG. 8J is a cross-sectional view. FIG. 8K is a top view. FIG. 8L shows a variety of possible shapes of the distal end of the distal portion, laid out on a flat. FIG. 8M shows a view illustrating certain dimensional parameters of the cross-section of the distal portion. FIG. 8N shows certain other dimensional parameters of the cross-section of the distal portion. FIG. 8O shows a blade in which the concavity of the gripping portion and the concavity of the distal portion face in opposite directions. FIG. 8P shows a blade in which the distal portion is rotated by a slight angle with respect to the gripping portion. FIGS. 8Q and 8R are cross-sections of FIG. 8P.

FIG. 9A-9F are views of a splash guard.

Figure 10A:
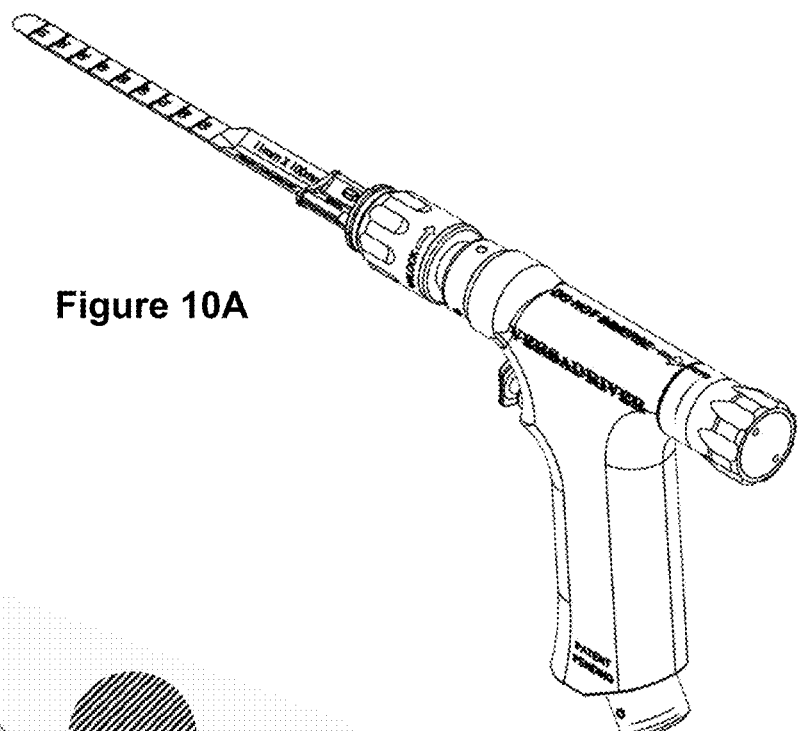
Figure 10B:
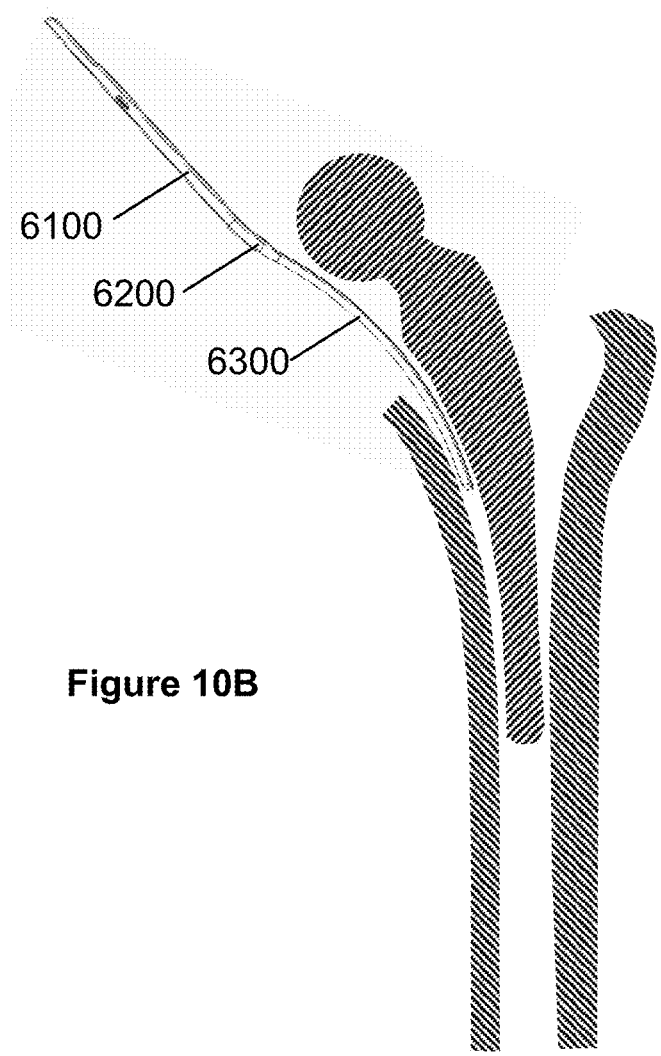

FIG. 10A shows a blade of an embodiment of the invention in combination with a power tool or driving device. FIG. 10B shows a blade of an embodiment of the invention being used during a revision surgical procedure to detach an implant from a bone.

DETAILED DESCRIPTION OF THE INVENTION

Figure 1A:
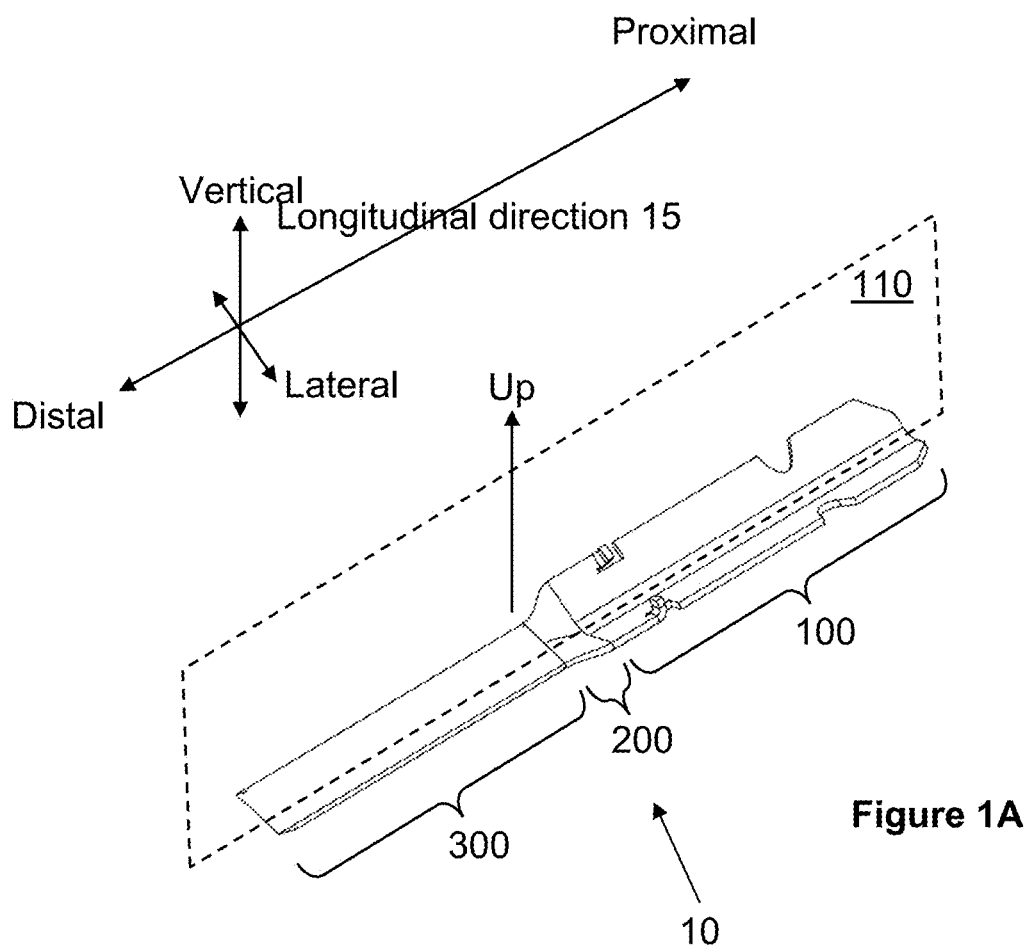

In embodiments of the invention, and referring now to FIGS. 1A-10B, there may be provided a blade 10. In FIG. 1A, directions are labeled on a generic blade as in the parent U.S. Pat. No. 10,595,879. In discussions herein, the term proximal is used to refer to the end of the blade closest to the hand of the user. Distal is used to refer to the end of the blade where cutting of a material at the surgical site takes place, opposite to the proximal end. The blade 10 may comprise, in sequence, a gripping portion 100, a transition portion 200, and a distal portion 300 which may be a cutting portion. Gripping portion 100 may have a longitudinal direction. In embodiments that are generally straight, the blade 10 as a whole may have a longitudinal direction that is coincident with the longitudinal direction of the gripping portion 100. Blade 10, or at least gripping portion 100, may have a plane of symmetry 110 as shown in FIG. 1. An upward direction, with respect to a blade 10, may be defined as perpendicular to a flat surface of a blade 10 if a blade 10 has a flat surface, or a direction that is toward the interior of a concave surface of the blade 10.

Blade 10 may be suitable to deliver force to whatever material the distal end of the blade 10 contacts. Such force may be compressive in nature and may be either static or dynamic, and could be of the nature of a rapidly applied impact force. In various embodiments, the cutting portion or distal portion may be either planar or non-planar. At whatever edge or edges of blade 10 are desired, the distal portion may have a cutting edge, which may be distally located, that is suitable to cut a material such as bone, or bone cement in the case of revision surgery. Any cutting edge may be sharp, or may be serrated, or may have a combination of these features or still other features. As illustrated, the two side edges of the distal portion are not sharp, although they could be sharp if desired. The gripping portion may be complementary to or suitable to engage with a chuck or similar component of the driving device.

Blade that is Longitudinally Straight, Having a Distal Portion that is a Cutting Portion that is Flat, and Having a Multi-Region Transition Portion In an embodiment of the invention, referring now to FIGS. 1B-1G, a blade 10 may comprise, in sequence, a gripping portion 1100 followed by a transition portion 1200 followed by a distal portion 1300. The transition portion 1200 may be continuous with the distal portion 1300, and the gripping portion 1100 may be continuous with the transition portion 1200.

In FIGS. 1B-1G, the distal portion 1300 is illustrated as being planar or substantially planar. The distal portion 1300 is illustrated as having a distal portion planar surface facing in an upward direction. The distal portion 1300 may have a flat surface extending from one lateral side to another opposed lateral side. At whatever edge or edges are desired, the distal portion 1300 may have an edge that is suitable to cut a material. Distal portion 1300 is illustrated as being generally rectangular except at the cutting edge 1320. However, other shapes could also be used if desired.

Figure 1B:
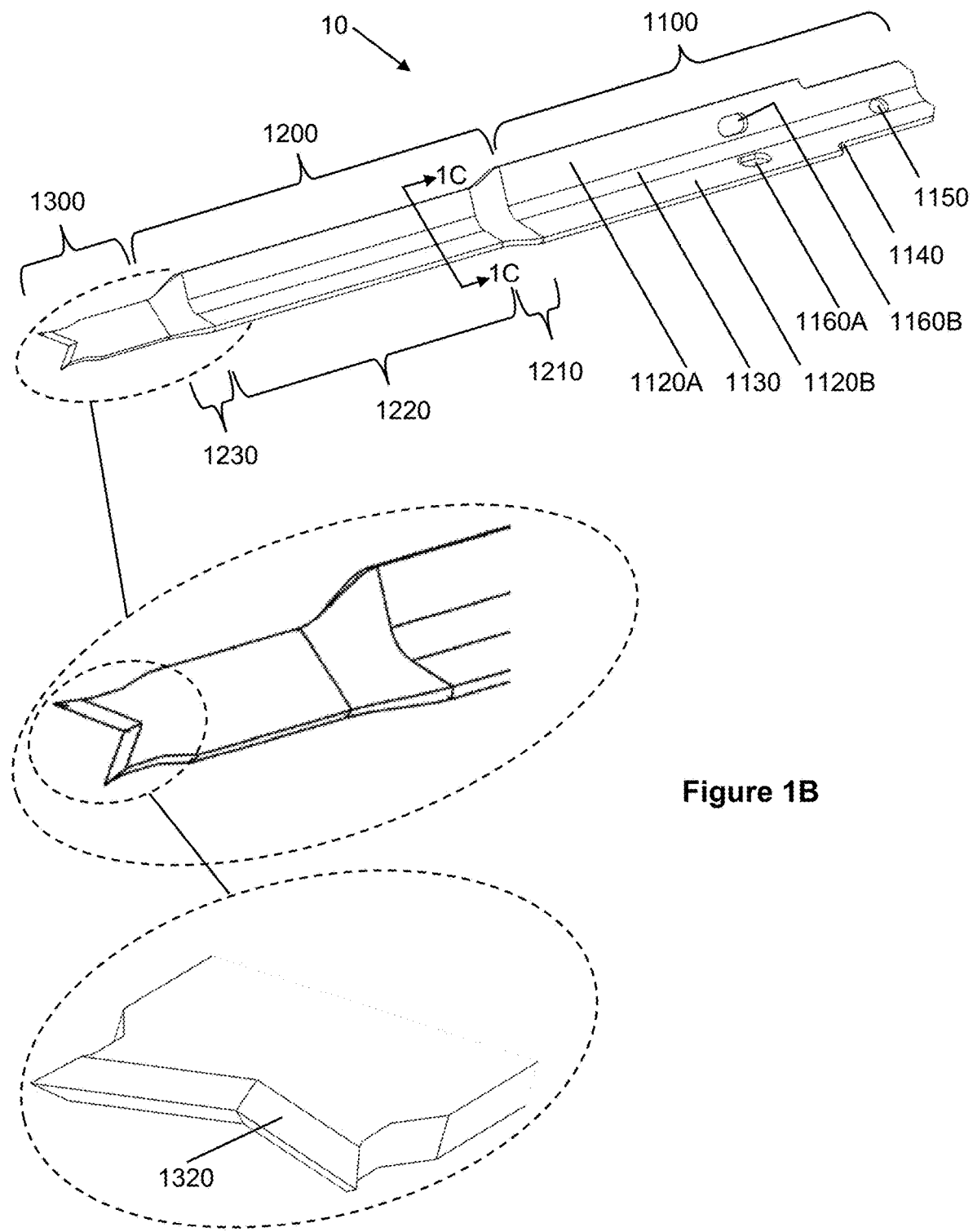

Distal portion 1300 may have at least one cutting edge 1320, which may be distally located on the blade 10. Cutting edge 1320 may be adapted for cutting such as by being beveled, for example. Any cutting edge may be sharp, or may be serrated, or may have a combination of these features or still other features. As illustrated, the cutting edge 1320 or distal end of distal portion 1300 has a sharp edge that is located at the middle of the thickness of distal portion 1300. However, other placements are also possible with respect to the thickness of the distal portion 1300. In FIG. 1B, the distal portion 1300 is illustrated as having a distal configuration that is a forked or serpent-tongue configuration. It can be understood that it is not essential that the distal end 1300 have the illustrated forked or serpent-tongue configuration. Other shapes of the cutting end 1300 are also possible, such as straight or having simple curvature (either concave or convex).

As illustrated, the two side edges of distal portion 1300 are not sharp, although they could be sharp if desired.

Gripping portion 1100 may have various surfaces. Gripping portion 1100 may have two edges, which may extend at least approximately or partially parallel to the longitudinal direction of gripping portion 1100. Along these edges may be surfaces that may be termed minor surfaces, which may correspond to the thickness of sheet material of which the blade may be formed. There may also be major surfaces that extend generally from one edge to the opposed edge of gripping portion 1100. The major surfaces may generally have larger surface area than the corresponding minor surfaces. The major surface may be a surface that does not entirely lie in a single plane. Gripping portion 1100 may be concave, and for purposes of description the direction in which gripping portion 1100 is concave may be termed an upward direction. For example, for a cross-section taken with a sectioning plane that is perpendicular to the longitudinal direction of the gripping portion 1100, gripping portion 1100 may have a cross-sectional shape that is a "V" shape having either a pointed vertex or a rounded vertex. The "V" shape may comprise two flat sides 1120A, 1120B. The two flat sides 1120A, 1120B of the "V" shape may define an included angle $\alpha_g$ as labeled in FIG. 1C. Possible values of this included angle range from 90 degrees to 150 degrees, with atypical value of 120 degrees. There may further be provided a bottom portion 1130 of the "V" shape, which may be rounded. Still other cross-sectional shapes of gripping portion 1100, not lying entirely in a single plane, are also possible.

The shape of gripping portion 1100 may be complementary to a chuck or similar component that holds gripping portion 1100, with the chuck or similar component being capable of transmitting load to or receiving load from the gripping portion 1100.

Figure 1C:
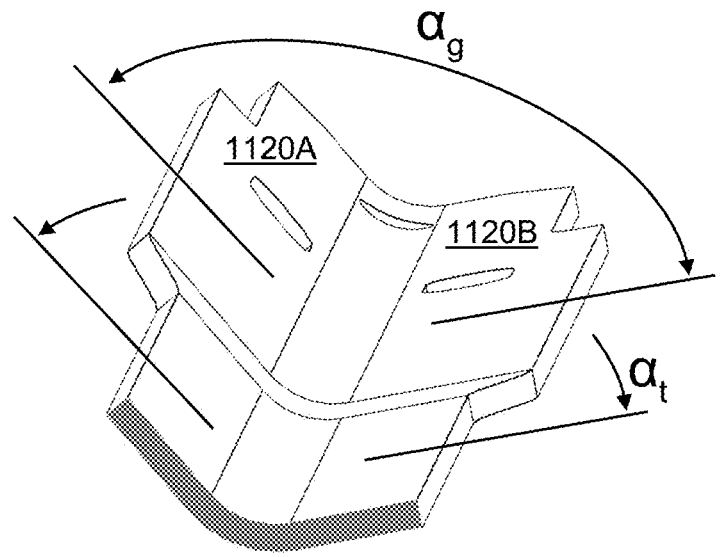
Figure 1D:
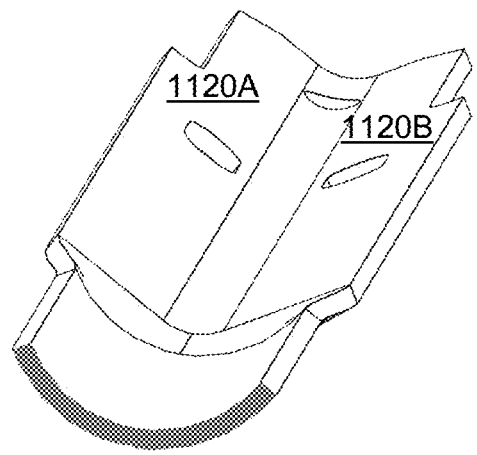
Figure 1E:
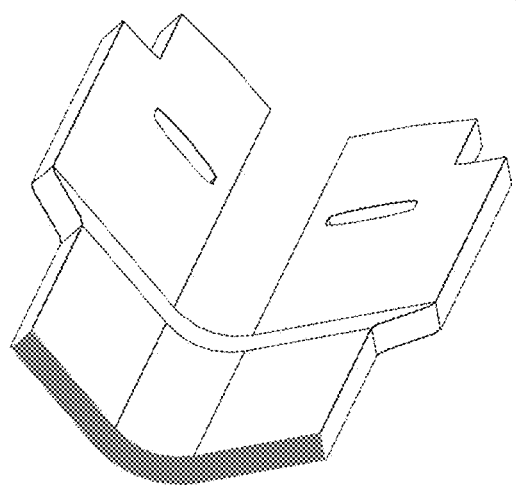

It is still further possible the gripping portion 1100 could have a shape that comprises the two legs 1120A, 1120B of the "V" while not having the connecting portion or vertex of the "V" that in other illustrations is illustrated as connecting the two legs of the "V." In such an embodiment, the gripping portion 1100 may comprise two legs each of which is generally parallel to the longitudinal direction of the gripping portion 1100 but are separate from each other for at least a portion of the gripping portion 1100. Such a configuration is illustrated in FIG. 1E.

Gripping portion 1100 may further comprise a shoulder feature 1140, which may be located at or near the proximal end of the gripping portion 1100. Shoulder feature 1140 may comprise cutouts as illustrated, or other appropriate shape. Shoulder feature 1140 may be complementary to a feature of the chuck or similar component. The interaction of shoulder feature 1140 and the complementary feature of the chuck or similar component may be suitable to transmit load in an axial direction that is compressive along the longitudinal direction of blade 10.

In the gripping portion 1100, there may further be provided holes as may be desired. Such holes may be circular, racetrack-shaped, or any other shape as may be desired.

Such holes or similar features may be suitable for any of: engagement with neighboring components, geometric registration, or force transmission.

There may be provided a hole 1150, which may be located on the centerline of the gripping portion 1100. Hole 1150 is illustrated as being round although other shapes are possible. Such hole 1150 may be such as to engage with a pin or similar engaging component of the handpiece or chuck or similar driving device that drives the blade 10. Such hole 1150 and engagement therewith may provide retention of the blade 10 in the chuck or similar component, and may also serve as a positioning or geometric registration feature, and may also serve to transmit force along the axial direction of the blade 10 from the chuck or similar component to the blade 10. It is also possible that, for any of these purposes, the chuck or similar component could engage with the external boundary of the gripping portion 1100 of blade 10, for example, such as shoulder 1140, or with still other features of the blade 10.

Holes 1160A, 1160B may also be provided. Holes 1160A, 1160B may be located one in each arm of the "V" and may be located symmetrically with respect to each other around a central longitudinal plane of symmetry. For example, such holes may be suitable to engage with a splash guard (described elsewhere herein). Holes 1160A, 1160B are illustrated as being racetrack-shaped, although other shapes are possible. Holes 1160A, 1160B are illustrated as being generally perpendicular to the local flat surfaces 1120A, 1120B of the "V" shape. However, it is alternatively possible that such holes could be aligned in the vertical direction of the blade 10, or could have still other orientation as may be desired.

It would also be possible to provide still other features such as tabs, or holes of non-circular shapes, slots, etc., wherever desired.

In regard to transition portion 1200, transition portion 1200 may transition between the shape of gripping portion 1100 and the shape of distal portion 1300. In an embodiment, transition portion 1200 may have an upward-facing surface that is three-dimensional and does not entirely lie in a single plane.

As illustrated, the transition portion 1200 may comprise several sub-regions. There may be, in sequence, a first transitional sub-region 1210, and a mid-region 1220, and a second transitional sub-region 1230. The first transitional sub-region 1210 may be continuous with the gripping portion 1100, and the second transitional sub-region 1230 may be continuous with the distal portion 1300.

Mid-region 1220 may have an upward-facing surface that does not entirely lie in a single plane. Mid-region 1220 may be concave when viewed from above. Mid-region 1220 may have a cross-sectional shape that repeats itself over some distance along the longitudinal direction of gripping portion 1100 or transition portion 1200, in the manner sometimes referred to as extrusion. For example, mid-region 1220 may have a cross-sectional shape that is a "V" shape having either a pointed vertex or a rounded vertex. Mid-region 1220 is illustrated in FIG. 1C as being V-shaped with an included angle of $\alpha_r$. Alternatively, mid-region 1220 may be trough-shaped, i.e., having a cross-sectional shape that is continuously curved as shown in FIG. 1D.

First transitional sub-region 1210 and second transitional sub-region 1230 may have upward-facing surfaces that are three-dimensional and do not entirely lie in a single plane.

In an embodiment, the gripping portion 1100 may have a gripping portion width W1, the mid-region 1220 may have a mid-region width W2, and the distal portion 1300 may have a distal portion width W3, and the gripping portion width may be greater than the mid-region width and the mid-region width may be greater than the distal portion width.

In an embodiment, the gripping portion 1100 may have a gripping portion height H1, the mid-region 1220 may have a mid-region height H2, and the distal portion 1300 may have a distal portion height H3, and the gripping portion height may be greater than the mid-region height and the mid-region height may be greater than the distal portion height.

In a side view of blade 10, as shown particularly in FIG. 1G, distal portion 1300 can have a thickness "t" in what may be considered a vertical dimension. In the same vertical direction, gripping portion 1100 may have a vertical dimension (top extreme to bottom extreme) that is greater than thickness "t." Gripping portion 1100 may have an upper extreme bounding plane that is parallel to the longitudinal axis 15 and just touches an extreme uppermost feature of gripping portion 1100. Similarly, gripping portion 1100 may have a lower extreme bounding plane that is parallel to the longitudinal axis 15 and just touches an extreme lowest feature of gripping portion 1100.

Similar to convention with gripping portion 1100, distal portion 1300 may have surfaces designated as minor surfaces (running along the edges of distal portion 1300) and may have major surfaces (connecting an edge of distal portion 1300 to an opposed edge of distal portion 1300).

In an embodiment, the distal portion 1300 may have a distal portion thickness and the transition portion 1200 may have a vertical dimension, and a ratio of the vertical dimension to the distal portion thickness may be in a range of from 2:1 to 10:1. In an embodiment, the distal portion 1300 may have a distal portion thickness and the transition portion 1200 may have a proximal-distal dimension, and a ratio of the proximal-distal dimension to the distal portion thickness may be in a range of from 2:1 to 10:1. In an embodiment, the transition portion 1200 may have a proximal-distal dimension and the transition portion 1200 may have a vertical dimension, and a ratio of the vertical dimension to the distal portion thickness may be in a range of from 2:1 to 1:2.

As best illustrated in FIG. 1G, in an embodiment of the invention, the distal portion 1300 may be disposed such that its lower extreme bounding plane coincides with the lower extreme bounding plane of gripping portion 300. More generally, the distal portion 1300 may be disposed anywhere between the upper extreme bounding plane of gripping portion 1100 and the lower extreme bounding plane of gripping portion 1100. However, even this relation is not essential. The vertical placement of distal portion 1300 could have any desired relation to the vertical placement of gripping portion 1100. In fact, if desired, it is even possible that the distal portion 1300 could be outside of the range that is defined by the upper extreme bounding plane of the gripping portion 1100 and the lower extreme bounding plane of the gripping portion 1100, even if the distal portion 1300 and the gripping portion both extend generally along a common longitudinal axis 15.

It is believed, although it is not wished to be limited to this explanation, that the presence of a transition portion 1200 as just described and illustrated provides a combination of providing reasonably good stiffness while still not occupying a lot of space, thereby providing a good combination of providing reasonably good stiffness while allowing the blade to access internal spaces that are long and narrow or hard to reach. During use, the blade 10 may function to carry compressive load along its lengthwise direction during certain parts of the loading cycle that it experiences. The compressive load may serve to perform the intended purpose of the blade 10, namely, to deliver impact force at the tip of the blade so as to chip away bone or bone cement such as during orthopedic revision surgery. It is believed, although it is not wished to be limited to this explanation, that if a transition portion 1200 had a more planar geometric nature it would be more likely to buckle or bend upon application of compressive force, or to transmit such compressive force less efficiently to the tip that is in contact with the solid material that is desired to be chipped or cut.

Blade that is Longitudinally Straight, Having a Distal Portion that is Non-Planar, Such as Curved, with the Distal Portion being a Cutting Portion Another embodiment of the invention is illustrated in FIGS. 2A-2I. Similar to other embodiments, this embodiment of blade 10 may comprise, in sequence, a gripping portion 2100 followed by a transition portion 2200 followed by a distal portion 2300. The transition portion 2200 may be continuous with the distal portion 2300, and the gripping portion 2100 may be continuous with the transition portion 2200.

Figure 2H:
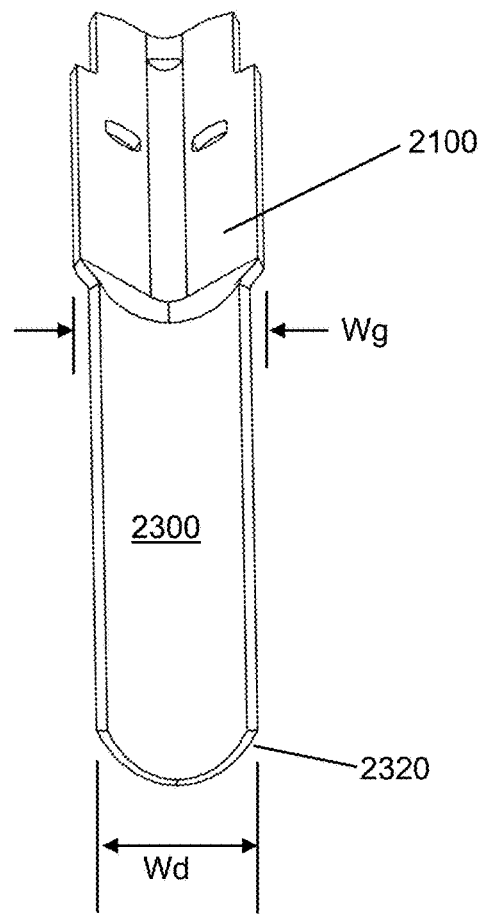

As illustrated in FIGS. 2A-2I, distal portion 2300 may extend along an axis that is generally straight. In this embodiment, the distal portion 2300 may have a cross-sectional shape (with respect to a cutting plane that is perpendicular to the longitudinal direction of blade 10) that does not lie in a single plane. As illustrated especially in FIGS. 2B and 2G, the distal portion 2300 may have a cross-sectional shape that is curved having a concave aspect, and a first direction may be defined as proceeding away from the concave surface of the distal portion 2300. This first direction may be considered an upward direction although such designation may depend on how the blade is used. As illustrated in FIGS. 2B, 2G, a cross-section of distal portion 2300 may have a trough shape that is curved, which may be an arc of a circle. Other cross-sectional shapes are also possible.

Distal portion 2300 may have at least one cutting edge 2320, which may be distally located on the blade 10. Cutting edge 2320 may be adapted for cutting such as by being beveled, for example. Any of various end contours are possible.

Referring now to the gripping portion 2100, gripping portion 2100 may have an upward-facing surface that faces generally in the first direction or upward direction, and the first-direction-facing or upward-facing surface might not entirely lie in a single plane. Gripping portion 2100 may be concave when viewed from above, and may have a cross-sectional shape that is a "V" shape having either a pointed vertex or a rounded vertex or no vertex. Gripping portion 2100 may have a shape that is complementary to a chuck or similar device that holds gripping portion 2100 and is capable of transmitting or receiving load to or from the gripping portion 2100. Features of gripping portion 2100 may be similar or identical to those of gripping portion 1100.

The concave nature of distal portion 2300 and the concave nature of gripping portion 2100 may both be concave in the same general direction as each other, i.e., both of them being upward-facing as directions are described herein. The cross-sectional shape of distal portion 2300 and the cross-sectional shape of gripping portion 2100 may be different from each other in some geometric respect. For example, gripping portion 2100 may have a cross-sectional shape that is "V" shaped with either a round vertex or a pointed vertex, while distal portion 2300 may have a cross-sectional shape that is continuously curved. A distal portion that is V-shaped is illustrated elsewhere herein.

Transition portion 2200 is described in FIG. 2D-2G, which contains cross-sections taken at various places. FIG. 2D shows the cross-sectional shape of the gripping region 2100, which is illustrated as V-shaped. FIG. 2E shows that near the gripping portion 2100, the transition portion 2200 has a cross-sectional shape that is nearly the "V" shape of the gripping region 2100. FIG. 2F shows that near the distal portion 2300, the transition portion 2200 has a cross-sectional shape that is nearly the curved or trough shape of distal portion 2300. Finally, FIG. 2G shows that the distal portion 2300 has a cross-sectional shape that is illustrated as curved or trough-shaped.

Gripping portion 2100 may have a gripping portion upper extreme bounding plane that is parallel to the longitudinal axis 15 and just touches an extreme uppermost feature of gripping portion 2100. Similarly, gripping portion 2100 may have a gripping portion lower extreme bounding plane that is parallel to the longitudinal axis 15 and just touches an extreme lowest feature of gripping portion 2100. Distal portion 2300 may have a distal portion upper extreme bounding plane that is parallel to the longitudinal axis 15 and just touches an extreme uppermost feature of distal portion 2300. Similarly, distal portion 2300 may have a distal portion lower extreme bounding plane that is parallel to the longitudinal axis 15 and just touches an extreme lowest feature of distal portion 2300. In an embodiment of the invention, both distal portion upper extreme bounding plane and distal portion lower extreme bounding plane both may lie between (or be coincident with) gripping portion upper extreme bounding plane and gripping portion lower extreme bounding plane.

Figure 2I:
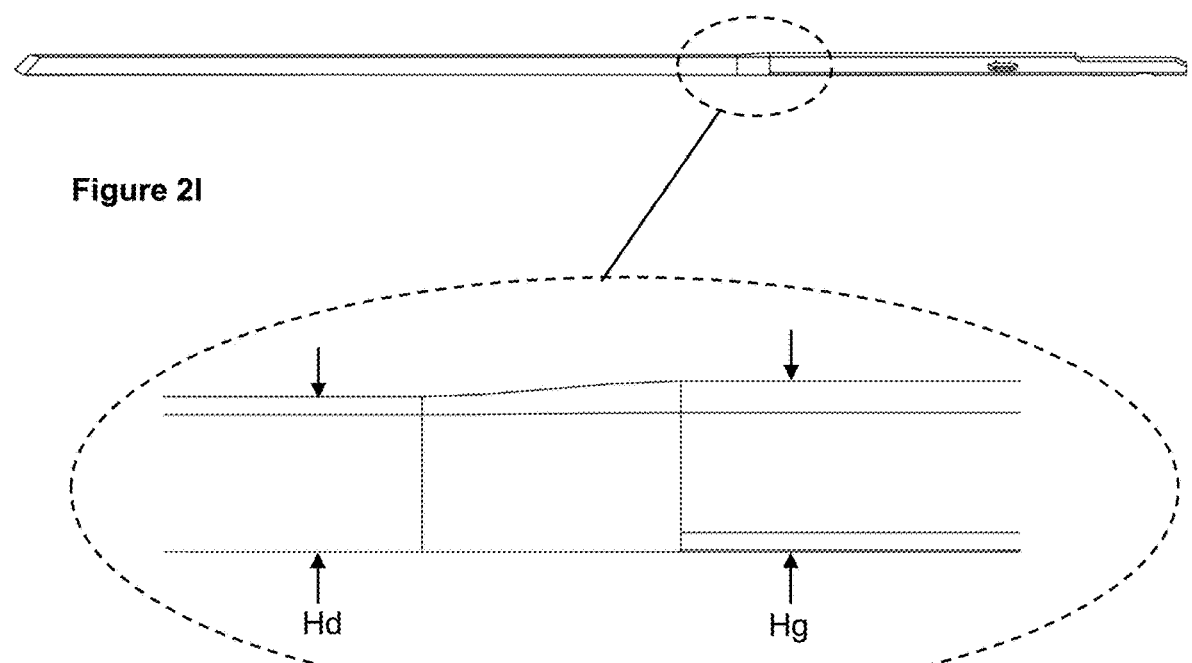

As illustrated in FIG. 2I, in an embodiment of the invention, the distal portion 2300 may be disposed such that its lower extreme bounding plane coincides with the lower extreme bounding plane of gripping portion 300. More generally, the lower extreme bounding plane of distal portion 2300 may be disposed anywhere between the upper extreme bounding plane of gripping portion 300 and the lower extreme bounding plane of gripping portion 300. Also, the upper extreme bounding plane of distal portion 2300 may be disposed anywhere between the upper extreme bounding plane of gripping portion 300 and the lower extreme bounding plane of gripping portion 300.

Even more generally, the vertical placement of distal portion 2300 could have any desired relation to the vertical placement of gripping portion 2100. In fact, if desired, it is even possible that the distal portion 2300 could be outside of the range that is defined by the upper extreme bounding plane of the gripping portion 2100 and the lower extreme bounding plane of the gripping portion 2100, even if the distal portion 2300 and the gripping portion 2100 both extend generally along a common longitudinal axis 15.

In an embodiment, the gripping portion 2100 may have a gripping portion width Wg, and the distal portion 2300 may have a distal portion width Wd, and the gripping portion width may be greater than the distal portion width.

In an embodiment, the gripping portion 2100 may have a gripping portion height Hg, and the distal portion 2300 may have a distal portion height Hd, and the gripping portion height may be greater than the distal portion height.

As illustrated, the distal portion has a generally constant width locally everywhere except possibly in a small region near the tip (distal end). However, it is alternatively possible that some variation in width could occur along the longitudinal direction of the blade. It is possible that everywhere in the distal portion 2300, the local width of the distal portion 2300 may be smaller than the width of the gripping portion. If the width of the gripping portion is variable, it is possible that everywhere in the distal portion 2300, the local width of the distal portion 2300 may be smaller than the smallest width of the gripping portion 2100. It may still be true that the height of the gripping portion is greater than the height of the distal portion, or the width of the gripping portion is greater than the width of the distal portion in either an average sense or an overall sense.

Transition portion 2200 may transition between the cross-sectional shape of distal portion 2300 and the cross-sectional shape of gripping portion 2100. In an embodiment, transition portion 2200 may have an upward-facing surface that is three-dimensional and does not entirely lie in a single plane. As illustrated in FIGS. 2A-2I, the transition portion 2200 may transition from a cross-sectional shape of the gripping portion 2100 (illustrated as a rounded-V shape), to a cross-sectional shape of the distal portion 2300 (illustrated as a curved shape).

Figure 3:
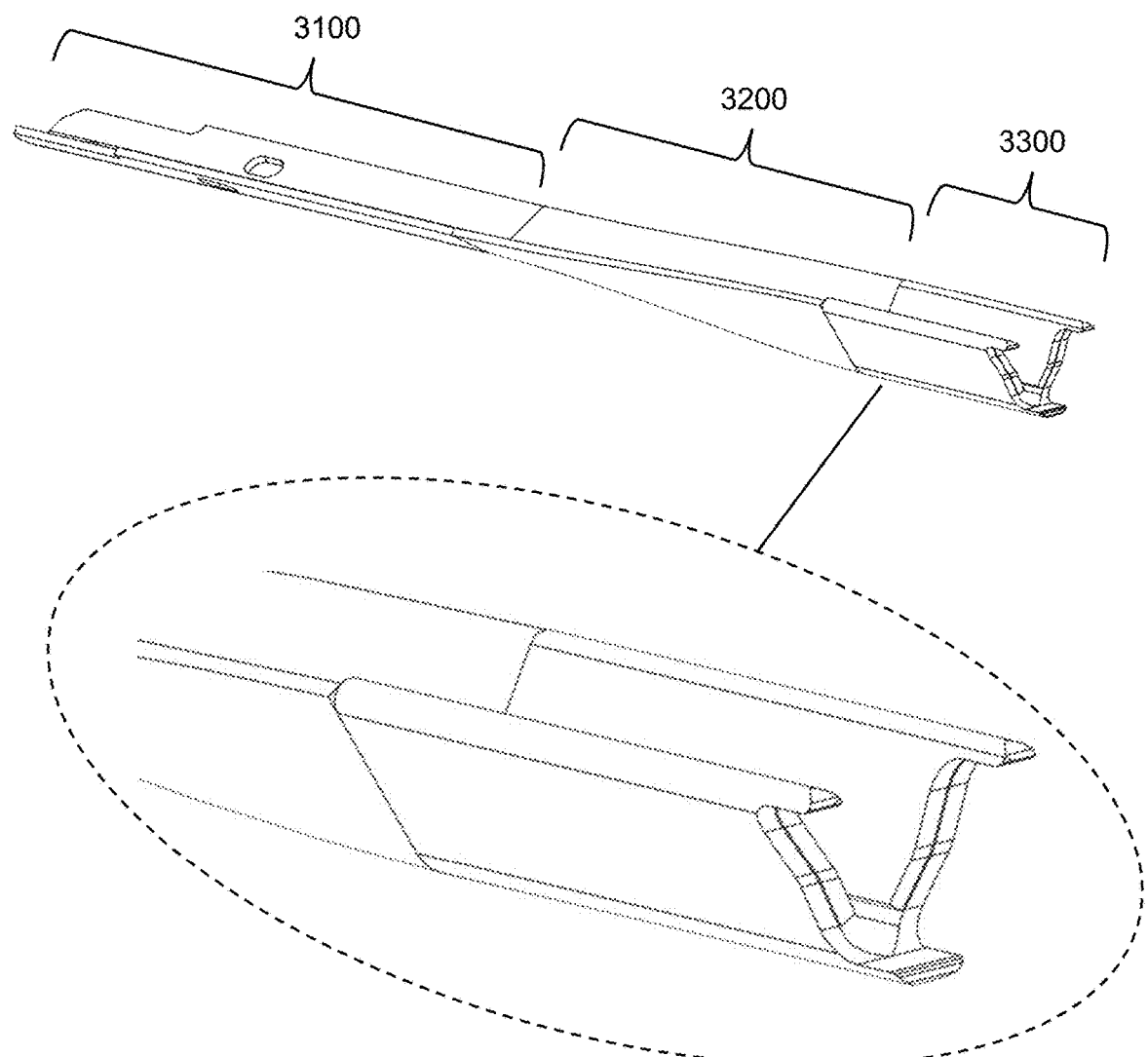
FIG. 3 is a three-dimensional view of a blade that is straight in the longitudinal direction, in which the distal portion has a cross-sectional shape that is V-shaped and the distal portion is adapted for pushing rather than for cutting.

Blade that is Longitudinally Straight, Having a Distal Portion that is Non-Planar, with the Distal Portion Optionally being Pushing but Non-Cutting Referring now to FIG. 3, similar to other embodiments, this embodiment of blade 10 may comprise, in sequence, a gripping portion 3100 followed by a transition portion 3200 followed by a distal portion 3300. The transition portion 3200 may be continuous with the distal portion 3300, and the gripping portion 3100 may be continuous with the transition portion 3200. Features not specifically described here may be in common with those of other analogous embodiments. In this embodiment, the distal portion 3300 may comprise features such that the blade 10 need not be intended as a cutting end as in some other embodiments, but rather may be intended as a pushing or gripping or locking end. This embodiment of blade 10 may lack a cutting edge, and instead, the geometry of the distal end of blade 10 may be generally blunt and if desired may further provide geometric registration or engagement with features of the implant thereby preventing the blade 10 from slipping off the edge of the implant.

In this embodiment, the distal portion 3300 is illustrated as having distal features that are generally blunt rather than sharp. The term "blunt" may be characterized as not sufficiently sharp to provide a cutting or chipping action with respect to bone or bone cement. The distal features may be appropriate to transmit force to an already-present implant urging the implant along a desired direction without performing any significant cutting or deformation of the surface of the implant. Furthermore, the distal portion 3300 may comprise distal features that are complementary to certain features of an implant of interest or may cooperate with certain features of an implant of interest. Such interaction may engage the distal end 3300 with the implant such as to maintain the blade 10 in contact with the implant or prevent the blade 10 from slipping off the implant such as in a sideways direction.

In this embodiment, gripping portion 3100 may have a gripping portion cross-section that may be V-shaped, and distal portion 3300 may have distal portion cross-section which may be a V-shaped cross-section. The distal portion cross-section of the distal portion 3300 may be different from the gripping portion cross-section of the gripping portion 3100, even if both cross-sections are generally some form of V-shape. For example, the included angles of the two "V" shapes may be different, or the radii of curvature at the tips of the "V" shapes may be different, or the lengths of the legs of the "V" shapes may be different.

In this embodiment, the transition portion 3200 is illustrated as being a transition from the gripping portion cross-section of the gripping portion 3100 (which may be the same gripping portion as in some other designs disclosed herein and may have a V-shaped cross-section) to a distal portion 3300 having a distal portion cross-section, which may have a V-shape that is different from the V-shape of the gripping portion 3100. Here, cross-sections are understood to be taken with respect to cutting planes that are perpendicular to the longitudinal direction 15.

This embodiment of blade 10 may be used during revision surgery after an implant (such as a knee implant) has been loosened from the bone using other blades such as other embodiments described herein. This embodiment of blade 10 may be used to impart force to the implant (not illustrated) to finally unseat and remove the implant from the bone. In this embodiment, the end geometry of the distal portion 3300 may be used to maintain the blade 10 in contact with the implant without the blade 10 slipping off the implant, while the power tool or driving device and the blade 10 provide impact force to urge the implant away from its attachment and thereby loosen the implant. However, it can be understood that this embodiment of blade 10 also could be used in other situations and other anatomical locations.

As illustrated and described in FIG. 3, the V-shaped distal end 3300 is blunt for the described purpose. However, it is also possible that the distal end 3300 could have a sharp cutting edge as is described in other embodiments herein.

Figure 4A:
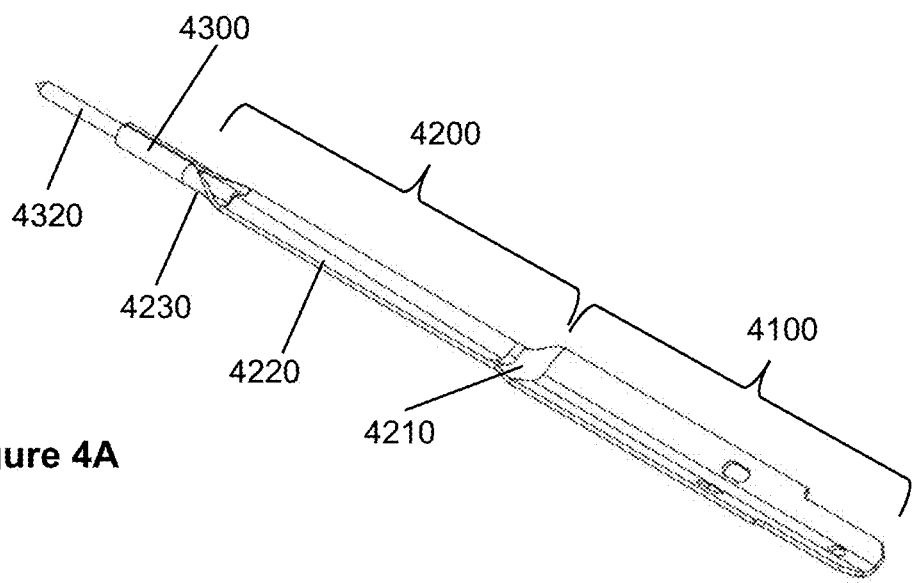
FIG. 4A is a three-dimensional view of a blade that is longitudinally straight, having a distal portion that contains an additional material in the form of a tip.
Figure 4B:
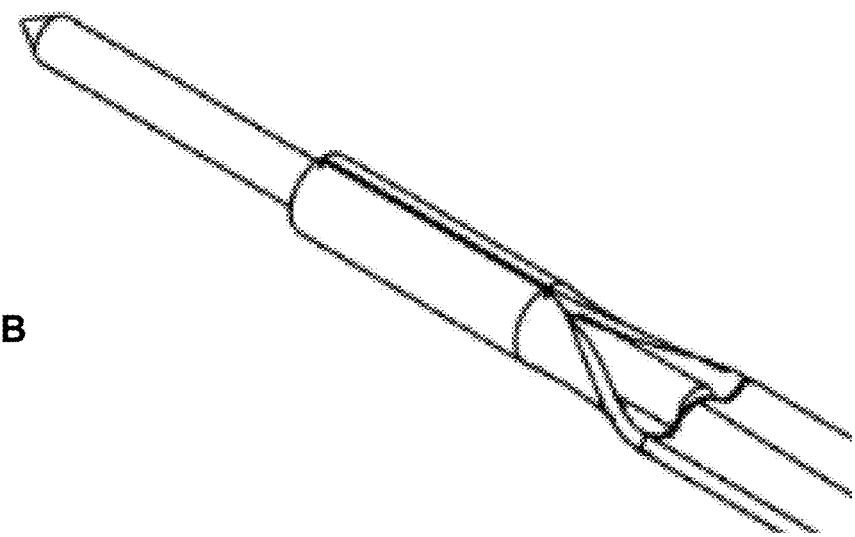
FIG. 4B is a close-up of FIG. 4A.

Blade that is Longitudinally Straight, Having a Distal Portion that Contains an Additional Material Another embodiment of the invention is illustrated in FIGS. 4A-4B. Similar to other embodiments, this embodiment of blade 10 may comprise, in sequence, a gripping portion 4100 followed by a transition portion 4200 followed by a distal portion 4300. The transition portion 4200 may be continuous with the distal portion 4300, and the gripping portion 4100 may be continuous with the transition portion 4200.

In this embodiment, the blade 10 may comprise a tip 4320 that is made of a material that is different from the material of the rest of the blade 10. For example, the tip 4320 may be made of a material that is especially hard, such as tungsten carbide. The tip 4320 may be generally cylindrical except for having at its most distal end a conical shape. The tip 4320 may be connected to the distal portion of the blade by having the distal portion of the blade wrapped around the tip 4320.

In this embodiment, the transition portion 4200 may comprise, a first transitional sub-region 4210 followed by a mid-region 4220 followed by a second transitional sub-region 4230. The mid-region 4220 itself may be non-constant in cross-section and may start out as having a trough shape cross-section and may end more distally as having a cross-sectional shape that is "W" shaped. The upwardly extending central part of the "W" shape may bear against the proximal end of the tip 4320. Such bearing relationship may be such as to transmit force of a compressive nature from the central part of the "W" to the proximal end of the tip 4320. Corners of the "W" may be rounded. The second transition sub-region 4230 may blend toward wrapping around the tip 4320. As illustrated, the mid-region 4220 is fairly long but it could be of any length.

Still further distally, the distal portion 4300 may be wrapped around the tip 4320 as part of a structural relationship between the blade 10 and the tip 4320.

The blade 10 of this embodiment may be used to help remove implants that have already been partially loosened using other blades. The tip 4320 of this embodiment may be directed against the already-present implant and the tip 4320 may be sharp enough and hard enough to gain purchase in the implant itself so the force of the handpiece can be transferred through the blade 10 to the implant to help detach the implant from the bone. Other uses may also be possible.

Figure 5A:
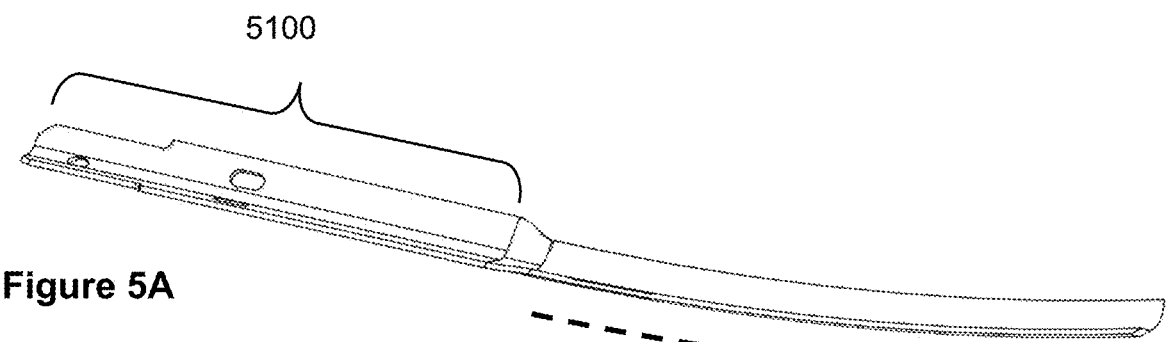
FIGS. 5A and 5B are three-dimensional views of a blade that is not straight but rather follows a path that is curved concavely.
Figure 5B:
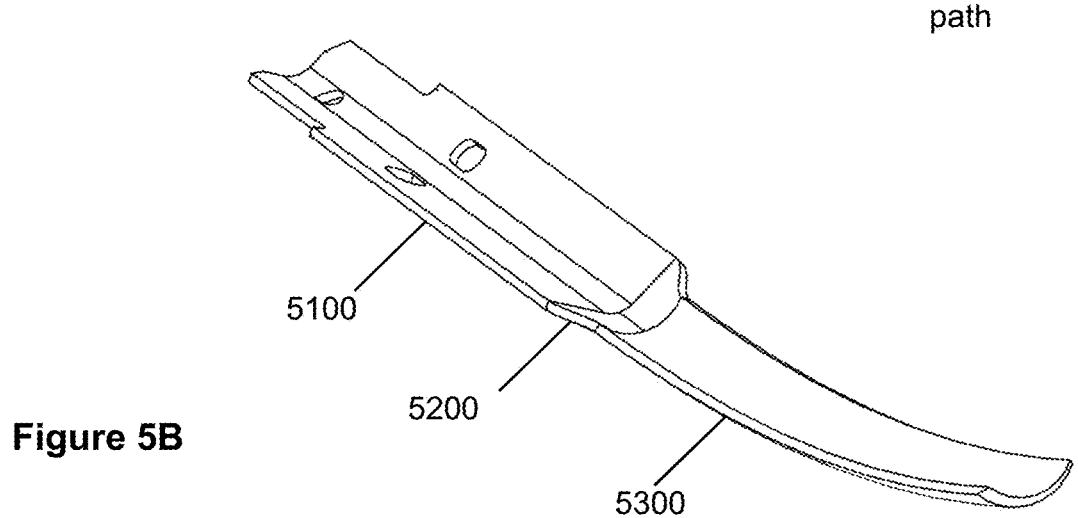

Blade that is Longitudinally Non-Straight, Having a Distal Portion that is Non-Planar, with the Distal Portion Longitudinally Having a Singly-Curved Path in a Concave Sense Referring now to FIGS. 5A-5B, similar to other embodiments, this embodiment of blade 10 may comprise, in sequence, a gripping portion 5100 followed by a transition portion 5200 followed by a distal portion 5300. The transition portion 5200 may be continuous with the distal portion 5300, and the gripping portion 5100 may be continuous with the transition portion 5200. Features not specifically described here may be in common with those of other analogous embodiments.

The distal portion 5300 may have a cross-sectional shape that is repeated by extending along a path, and in this embodiment the path need not be straight; rather, it can be curved. The path may be thought of as the intersection of the distal portion 5300 with the vertical plane of symmetry of the distal portion 5300, or any similar path along which the cross-sectional shape of the distal portion 5300 is carried along and reproduced to form the complete distal portion 5300. In an embodiment, the path may be located within a plane, which may be a plane of symmetry of gripping portion 5100. The path may have a local longitudinal direction that is a line that is tangent to that path at a particular point. In describing a local cross-sectional shape of the distal portion 5300, the distal portion 5300 may have a cross-sectional shape, with the cross-section being taken in a sectioning plane that is perpendicular to the local longitudinal direction of the blade.

For a distal portion 5300 that extends along a curved path as one proceeds along the lengthwise direction, the width dimension can be the local width dimension of a cross-section taken as just described. For a distal portion 5300 that extends along a curved path as one proceeds along the lengthwise direction, the local height dimension can be the local height dimension of a cross-section taken as just described.

As illustrated, the distal portion 5300 has a generally constant height locally everywhere except possibly in a small region near the tip (distal end). Alternatively, it is possible that some variation in height may occur along the longitudinal direction of the blade. If so, it is possible that everywhere in the distal portion 5300, the local height of the distal portion 5300 may be smaller than the height of the gripping portion 5100. If the height of the gripping portion 5100 is non-constant, it is possible that everywhere in the distal portion 5300, the local height of the distal portion 5300 may be smaller than the smallest height of the gripping portion 5100 (excluding localized interface features).

As illustrated, the distal portion 5300 has a generally constant width locally everywhere except possibly in a small region near the tip (distal end). Alternatively, it is possible that some variation in width may occur along the longitudinal direction of the blade 10. If so, it is possible that everywhere in the distal portion 5300, the local width of the distal portion 5300 may be smaller than the width of the gripping portion 5100. If the width of the gripping portion 5100 is non-constant, it is possible that everywhere in the distal portion 5300, the local width of the distal portion 5300 may be smaller than the smallest width of the gripping portion 5100 (excluding localized interface features).

The transition portion 5200 may transition from a cross-sectional shape that is a rounded-V shape cross-sectional shape of the gripping portion 5100, to a cross-sectional shape that is a curved shape. As illustrated in FIGS. 5A-5B, the transition portion 5200 may transition from a cross-sectional shape of the gripping portion 5100 (illustrated as a rounded-V shape), to a cross-sectional shape of the distal portion 5300 (illustrated as a curved shape).

In an embodiment, the curved path can be concave in the same sense that the distal portion cross-sectional shape is concave. This is illustrated in FIGS. 5A-5B. As illustrated, the path is concave in the same direction as the gripping portion 5100 is concave. In this embodiment, along the longitudinal direction of the blade 10, the distal portion 5300 of the blade 10 may be curved such that it curves towards the concave side of the gripping portion 5100 of the blade 10. This blade configuration may be termed the lateral hip blade, although it can be understood that this blade configuration also could be used in other anatomical locations.

Blade that is Longitudinally Non-Straight, Having a Distal Portion that is Non-Planar, with the Distal Portion Longitudinally Having a Path that is Curved in a Convex Sense In an embodiment, the curved path can be convex with respect to the direction that the distal portion cross-sectional shape is concave, or with respect to the gripping portion 6100 having a concave cross-section. This is illustrated in FIGS. 6A-6D. In this embodiment, along the longitudinal direction of the blade 10, the distal portion 6300 of the blade 10 may be curved such that its path curves away from the concave side of the gripping portion 6100 of the blade.

As illustrated, the path is straight in the gripping region 6100, then is concavely curved in the transition portion 6200, then has an inflection point which may be in the transition portion 6200, and then has concave curvature in the distal portion 6300. Other geometries are also possible.

As illustrated, the transition portion 6200 may have first transition region 6210 and second transition region 6220. In first transition region 6210, the path may deviate from the straight path that characterized the gripping portion 6100 while the width of first transition region 6210 may remain substantially equal to the width of gripping region 6100. In first transition region 6210, closest to the gripping portion 6100, there may optionally be geometric transition from one cross-sectional shape to another cross-sectional shape. In the second transition region 6220, the width of second transition region 6220 may transition from the width of gripping portion 6100 to the width of distal portion 6300, and in second transition region 6220 there may optionally be further transition of cross-sectional shape. Other geometries of transition are also possible.

This blade configuration may be termed the medial hip blade, although it can be understood that this blade configuration also could be used in other anatomical locations.

Offset Blade

Referring now to FIG. 7, similar to other embodiments, this embodiment of blade 10 may comprise, in sequence, a gripping portion 7100 followed by a transition portion 7200 followed by a distal portion 7300. The transition portion 7200 may be continuous with the distal portion 7300, and the gripping portion 7100 may be continuous with the transition portion 7200. Features not specifically described here may be in common with those of other analogous embodiments.

As illustrated, the transition portion 7200 may transition from a cross-sectional shape that is a rounded-V shape of the gripping portion 7100, to a cross-sectional shape that is a curved shape at the junction between the transition portion 7200 and the distal portion 7300. In this embodiment, the transition portion 7200 is illustrated as being longer (along the longitudinal direction of the blade) than it is in some of the other embodiments.

In this embodiment, the distal portion 7300, which is at the distal end of blade 10, is shown as having a geometry that could generally be described as an offset. In an embodiment, the distal portion 7300 may follow a path, and the path may be located within a plane, which may be a plane of symmetry of gripping portion 7100. In this embodiment, the path may first curve in one direction and then may curve in the opposite direction. The first curve may be described as convex and the second curve may be described as concave, with respect to the type of concavity defined by the gripping portion 7100. Furthermore, after executing the path having such sequential curvatures, the distal portion 7300 may further comprise an extreme distal segment 7350 that is substantially flat.

It is believed, although it is not wished to be limited to this explanation, that the presence of a transition portion 7200 and the particular shape of distal portion 7300 as just described and illustrated provides a combination of providing reasonably good stiffness while still not occupying a lot of space and providing access to certain anatomical geometries. This blade configuration may be termed the offset blade. This embodiment of blade 10 can be used to access the Posterior Cruciate Ligament Notch on the Tibial Plate and perform a cutting process to separate the tibial plate from the bone or the bone cement around the notch. This is a space that is very difficult to access without a specialized instrument. However, it can be understood that this blade configuration also could be used in other anatomical locations.

Cutting Edge of Blade

Figure 8A:
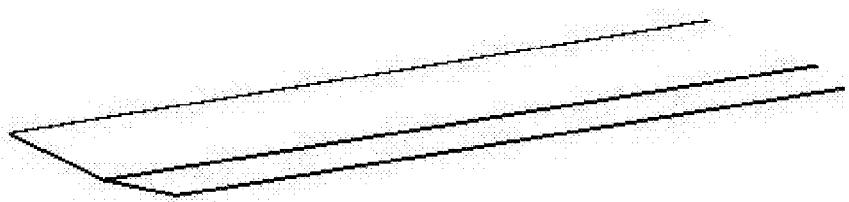
Figure 8B:
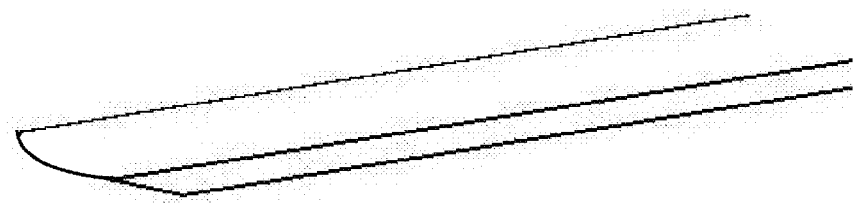
Figure 8C:
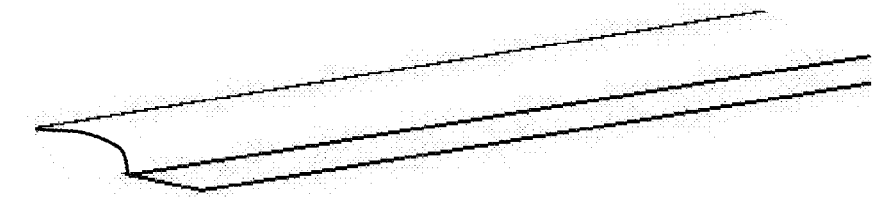
Figure 8D:
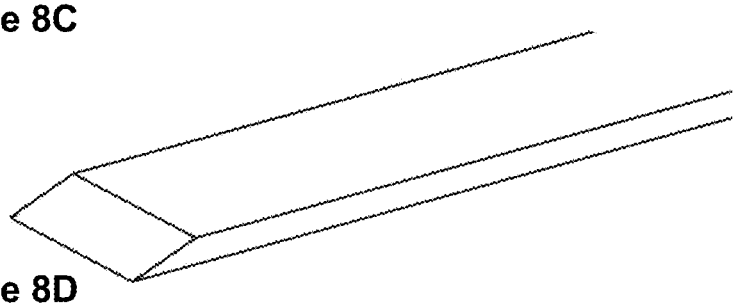
Figure 8E:
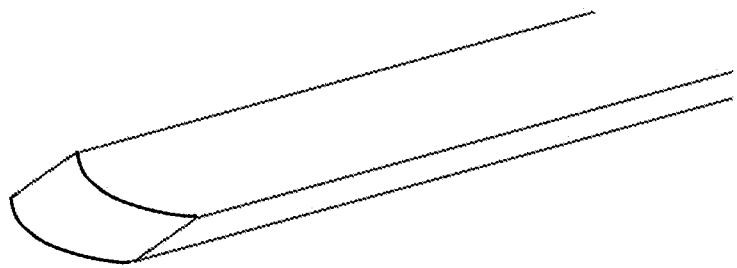
Figure 8F:
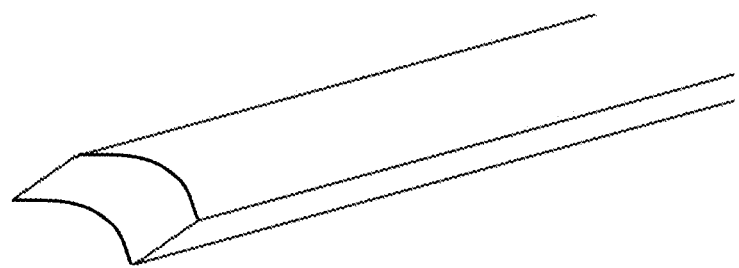
Figure 8G:
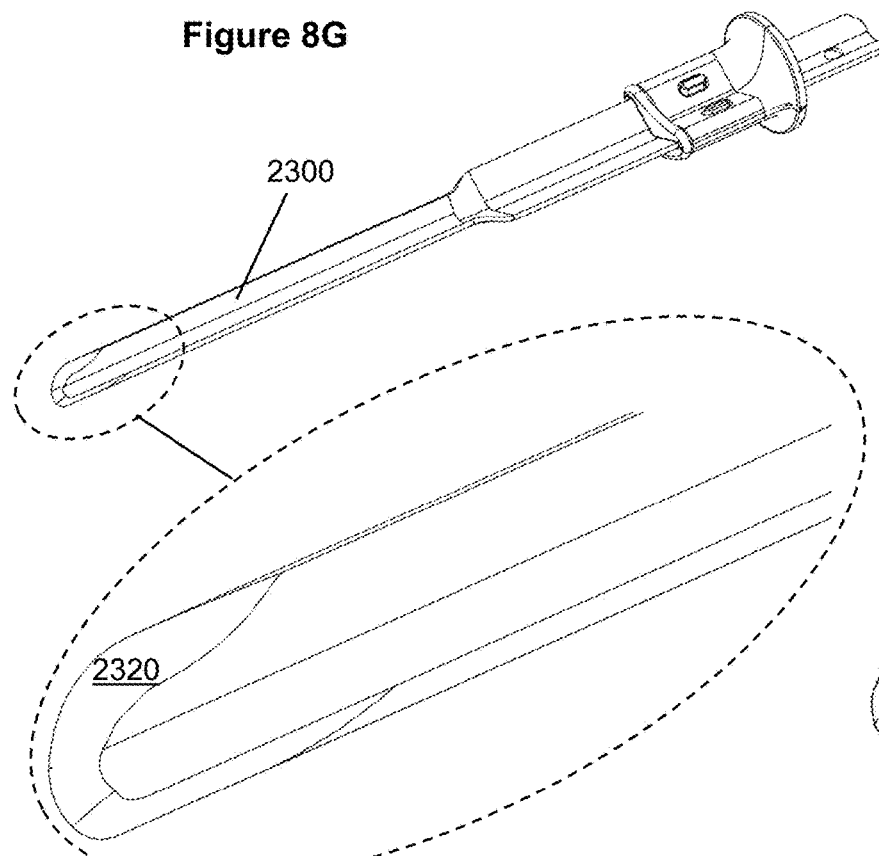
Figure 8H:
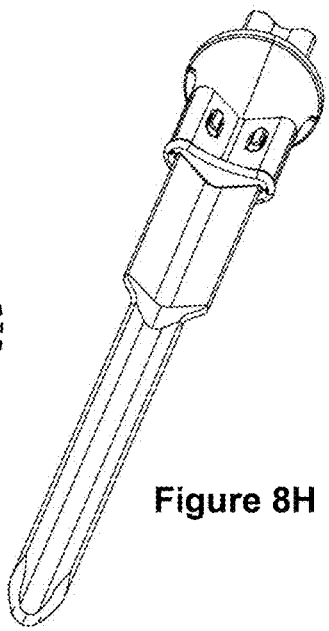
Figure 8I:
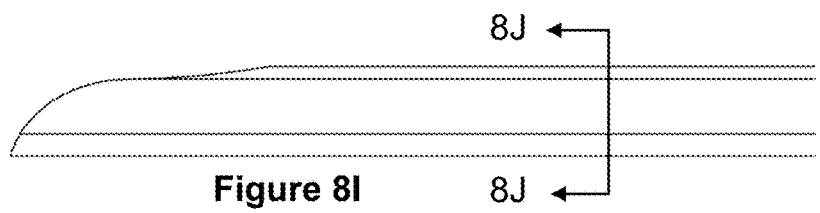
Figure 8J:
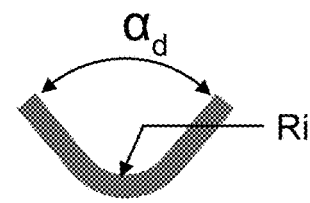
Figure 8K:
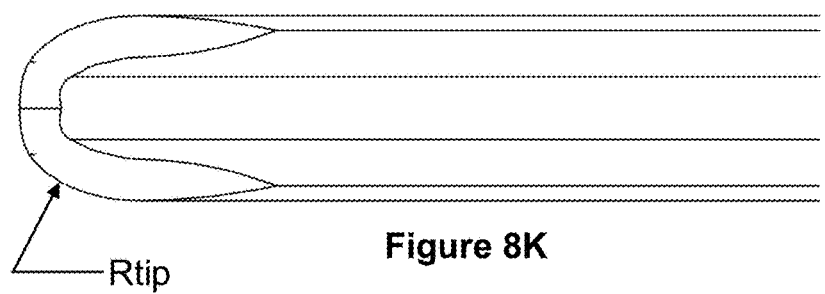
Figure 8L:
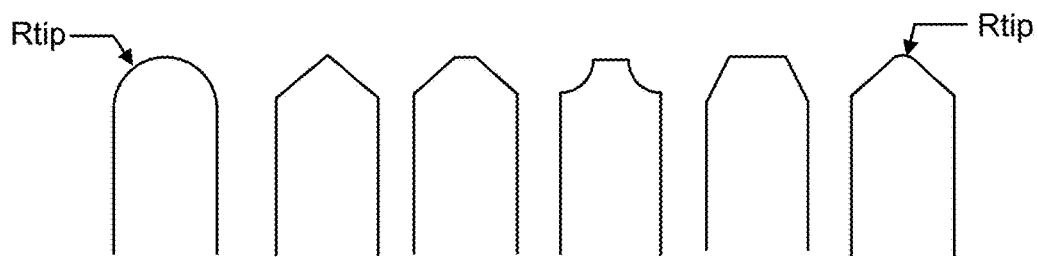
Figure 8M:
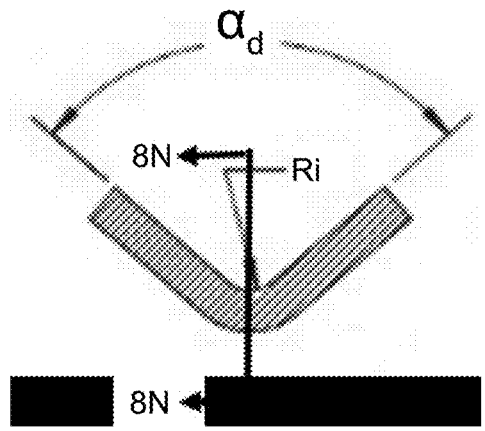
Figure 8N:
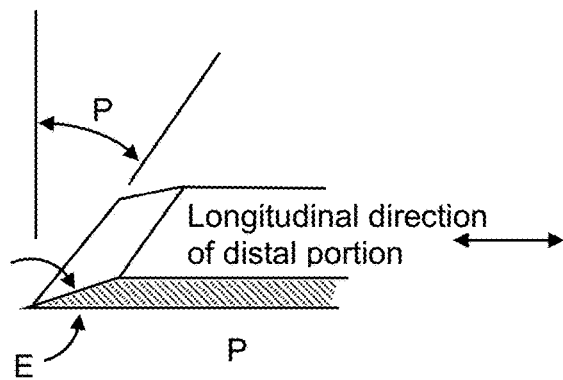
Figure 8O:
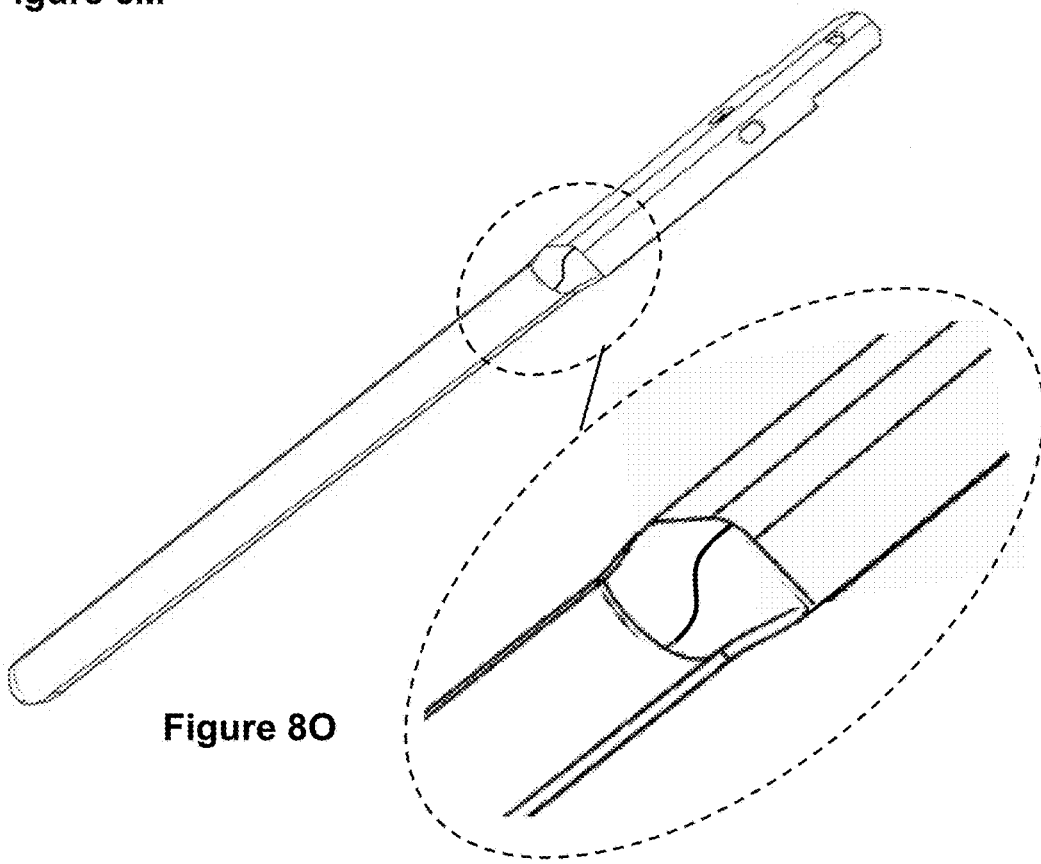
Figure 9A:
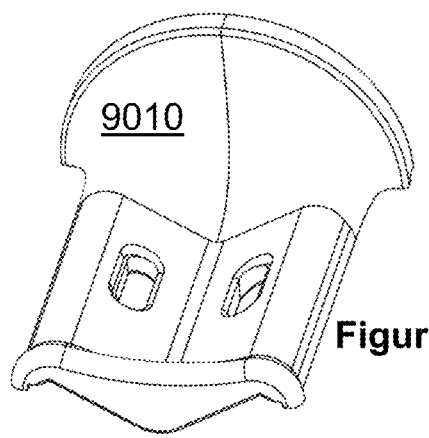
Figure 9C:
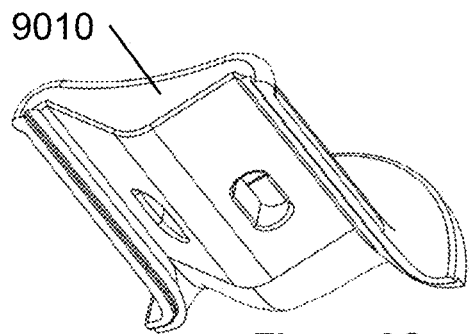
Figure 9B:
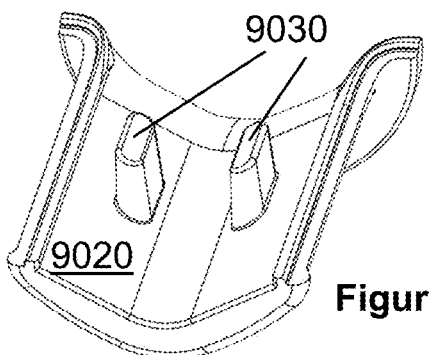
Figure 9D:
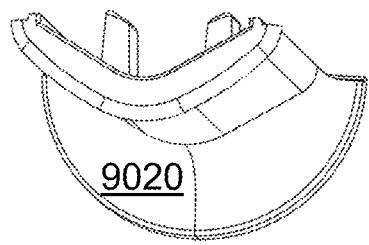
Figure 9E:
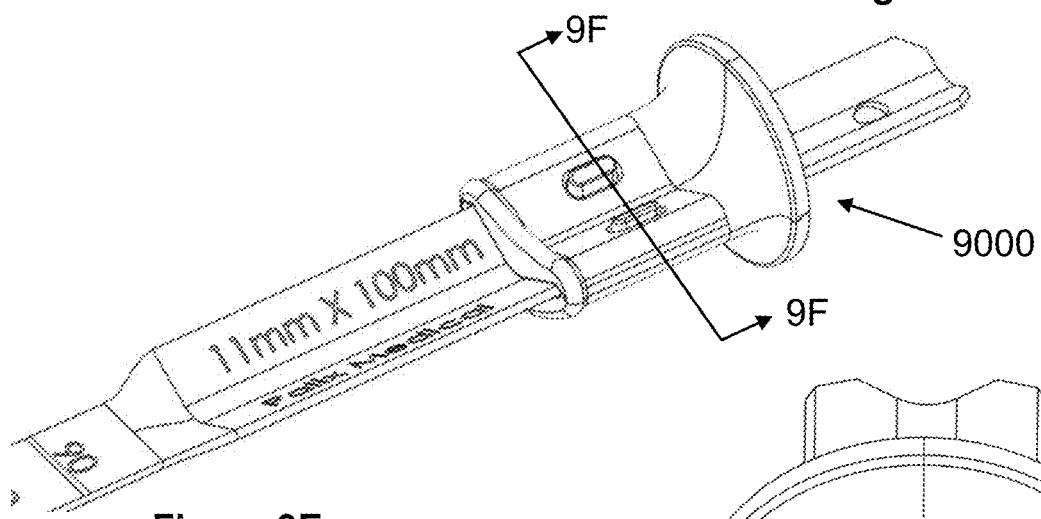
Figure 9F:
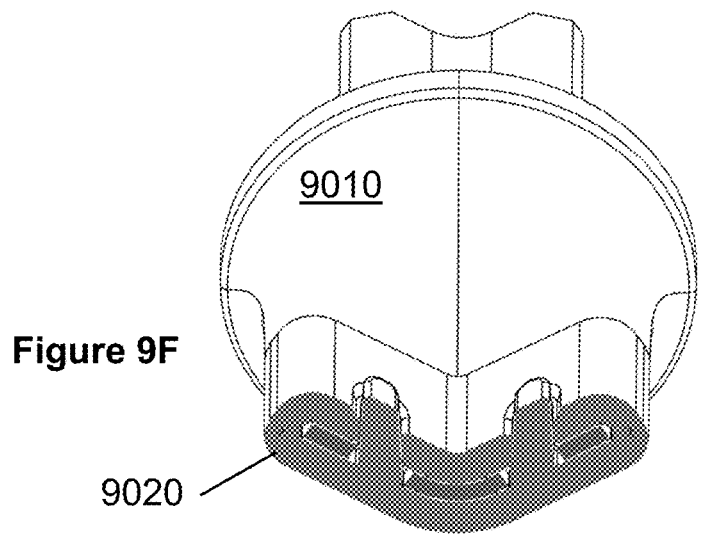

Referring now to FIGS. 8A-8K, distal portion 1300 (and 2300, 3300, 4300, 5300, 6300, 7300) may have a cutting edge 1320 that may be sharp or serrated or otherwise appropriate for cutting bone cement, bone or other tissue. Such cutting edge may have any of various geometries. FIGS. 8A-8F show a distal portion 1300 that is planar, with a variety of cutting edges. In FIGS. 8A-8C, the sharp cutting edge 1320 is contiguous with the upper surface of the distal portion 1300. In FIG. 8A, proceeding laterally from one side to the other along the cutting edge 1320, the cutting edge 1320 is straight. In FIG. 8B, the cutting edge 1320 is convex. In FIG. 8C, the cutting edge 1320 is concave. In FIGS. 8D-8F, the sharp cutting edge 1320 is contiguous with the lower surface of the distal portion 1300. In FIG. 8D, proceeding laterally from one side to the other along the cutting edge 1320, the cutting edge 1320 is straight. In FIG. 8E, the cutting edge 1320 is convex. In FIG. 8F, the cutting edge 1320 is concave.

FIGS. 8G and 8H illustrate a blade 10 in which the distal portion 2300 has distal portion cross-sectional shape that is a curved or rounded-V cross-sectional shape. FIG. 8I is a side view of the same blade. FIG. 8J is a cross-sectional view. FIG. 8K is a top view.

FIG. 8L shows views of various possible shapes of the distal end of the distal portion, if the blade were flattened out. The shapes illustrated in FIG. 8L can also be thought of as a starting blank early in the manufacturing process if the blade is formed by stamping or similar operation later in the manufacturing process. Some of the illustrated shapes have a tip radius Rtip. It is also possible that the tip could be semi-hexagonal as illustrated in FIG. 8L, or semi-octagonal. Still other tip configurations are possible using polygons of any other desired number of sides. Such polygons could be regular polygons (all sides and all angles being equal) as illustrated, or alternatively could be any other polygonal shape. The shape also could also be any multi sided geometry that approximates any of the other geometries shown.

With continued reference to FIGS. 8G-8K, the upper surface of the distal portion may have an internal radius of curvature Ri. Although the illustrated cross-section has a rounded-V shape having an internal radius of curvature near the vertex of the V, it is also possible for the cross-section to be continuously curved, such as an arc of a circle. An included angle $\alpha_d$ is defined as the angle between the respective legs of the "V" shape. For cross-sectional shapes that are other than a V, the angle can be defined as the angle between the tangent to the cross-sectional shape at one side and the tangent to the cross-sectional shape at the opposed side. It is further illustrated that sharp cutting edge 2320 is contiguous with the lower surface of the distal portion 2300. It is further illustrated that when viewed from above, the blade has a tip shape that is convex, and can be described by a radius of curvature Rtip. It is believed that these features in combination are particularly advantageous for cutting, especially for cutting bone cement. It can be useful to describe some of these parameters in terms of a ratio to another parameter. Typical values of some of these parameters may be: sharp cutting edge 2320 that is contiguous with the convex surface or lower surface of the distal portion 2300; a tip radius Rtip that is one half the width of the blade at the distal tip, or more generally Rtip being from one quarter the width of the blade to four times the width of the blade in the distal portion 1300; an internal radius Ri of approximately 0.09 inch, or more generally, from 0.03 inch to 0.25 inch; and an included angle "ad" of 80 degrees, or more generally, from 45 degrees to 160 degrees. Expressed in terms of a ratio, a suitable ratio of tip radius Rtip/inner radius Ri could range from 2 to 15.

FIG. 8N shows a longitudinal cross section of the distal end of distal portion 1300. The angle "P," is an angle that is visible in a top view and describes how a blade tip that is pointed "sweeps back" from the tip. A pressure angle "P" of zero would correspond to a flat-fronted blade as illustrated in FIGS. 8A and 8D, while a pressure angle "P" approaching 70 degrees would be sharply pointed. The pressure angle "P" influences how much pressure or local force is applied onto the material that is being cut or impacted. A small pressure angle, corresponding to a fairly blunt tip, will impart less pressure because the force applied by the blade would be distributed over a larger region. A larger pressure angle "P," corresponding to a more sharply pointed tip, can be expected to impart more localized pressure to the surface of the material being cut, because the force carried by the blade would be concentrated onto smaller region. The pressure angle "P" may be chosen to be between 20 and 90 degrees. FIG. 8N also shows the Edge angle "E" which is the angle the cutting edge is cut to (which relates to the removal of material by grinding, if a grinding process is used to manufacture the cutting edge). Angle "E" may be chosen to be between 5 and 60 degrees when the sharp edge is contiguous with either the top surface or the "bottom surface" of the distal portion 1300 (as in FIGS. 8A and 8D). If the cutting edge is not contiguous with either the top surface or the bottom surface (for example as shown in FIG. 1), the included angle between the surfaces that form the cutting edge may be chosen to be between 10 and 120 degrees. Still other geometries are also possible.

There are still other possibilities and embodiments in regard to blade shapes and spatial relationships among the gripping portion and the distal portion. As illustrated in FIG. 8O, it is possible that the gripping portion 8100 may be concave facing in one direction while the distal portion 8300 may be concave facing in a different direction. As illustrated in FIG. 8O, the directions of concavity are opposite each other. In this situation, the transition portion 8200 may be geometrically somewhat more complex than some of the other transition portions illustrated herein.

Even more generally, it is possible that, with respect to orientation around the longitudinal direction of the gripping portion 8100, the orientation of the gripping portion 8100 and the orientation of the distal portion 8300 could have any desired angular orientation with respect to each other. This is illustrated in FIGS. 8O-8R, in which the angular orientation of the distal portion 8300 is shown as being approximately 30 degrees away from the angular orientation of the gripping portion 8100. Also illustrated in FIG. 8R are geometric parameters Hg (height of the gripping portion), Wg (width of the gripping portion), Hd (height of the distal portion) and Wd (width of the distal portion). The width may be considered to be the dimension, in a direction that is approximately perpendicular to the local path, measured from one lateral edge of the portion to the opposite lateral edge of the portion. The height may be considered to be the dimension, in a direction that is approximately perpendicular to the local path, from one extreme bounding plane to an opposite extreme bounding plane. For example, one extreme bounding plane may touch both lateral edges of the portion of the blade. The other extreme bounding plane may pass through a point on the cross-section that is maximally distant from the first extreme bounding plane.

In embodiments of the invention, it is possible (although not required) that Hd (height of the distal portion) could be less than Hg (height of the gripping portion). In embodiments of the invention, it is possible (although not required) that Wd (width of the distal portion) could be less than Wg (width of the gripping portion). These geometric relationships may contribute to the gripping region (which during use is located further from the surgical site, where space is more available) being relatively stiff (such as in bending stiffness around any relevant axis of bending), and the distal portion might be slightly less stiff in order to better accommodate the limited space and dimensions available at or near the surgical site.

Other Components

Referring now to FIGS. 9A-9F, in an embodiment, there may also be provided a splash guard 9000. Splash guard 9000 may engage with blade 10, and specifically may engage with holes 1160A, 1160B. Splash guard 9000 may comprise an upper piece 9010 and a lower piece 9020 that are generally complementary with each other while fitting around blade 10 such as fitting around the gripping portion 1100 of blade 10. One of the pieces, such as lower piece 9020, may comprise two posts 9030, which may be receivable in corresponding apertures of upper piece 9010. Posts 9030 may be dimensioned to be receivable within holes in gripping portion 1100 such as holes 1160A, 1160B in gripping portion 1100. Splash guard 9000 may be made of a polymer such as rubber.

Blade 10 may be held in a chuck in a power tool or driving device. Any of various types of power tools or driving devices may be used. An exemplary power tool or driving device is shown in FIG. 10A. The power stroke on each actuation may be the direction that allows the blade to cut. Each actuation of the blade may cause an impact to the bone cement that the blade is in contact with. The powered handpiece can be powered by pneumatics or by electricity. Palix Medical's VersaDriver and Exactech's AcuDriver® are examples of powered pneumatic handpieces. DePuy Synthes' Kincise™ is an example of an electrically powered handpiece.

Use

An embodiment of the invention may also comprise a method of use. The blade 10 may be used in revision surgery in which an implant that has previously been implanted, possibly with the use of bone cement, needs to be removed. The blade 10 may have a distal end that is curved and shaped in a geometry that is somewhat similar to the exterior shape of the implant, or to the space between the implant and the bone. In general, the shape of the blade may be chosen to provide good access for separating bone cement from an implant, removing bone cement, bone, or other material. This is illustrated in FIG. 10B.

Further Comments

In an overall view of embodiments of the invention and their potential advantages, it can be useful to consider bending stiffness of a blade such as blade 10. In general, a shape that is out-of-plane such as a V-shape can be expected to have greater bending stiffness than a similar blade or blade portion that is planar. Such bending stiffness can refer to bending in the direction around an axis that lies in the lateral (side to side) direction of the distal portion or cutting portion of blade 10. Furthermore, although a typical direction of loading of the blade 10 may be along the longitudinal direction of blade 10, bending stiffness is relevant because bending stiffness contributes to the blade 10 being resistant to buckling upon application of compressive load along the longitudinal direction. Bending stiffness also is relevant in the event of any off-axis or sideways loads that might be experienced in particular surgical situations. The out-of-plane shape properties contribute to the moment of inertia parameter, as is conventionally used in calculations of bending and stress. This is true for the distal portion of a blade 10. Similarly, the bending stiffness of a transition portion can be expected to be greater than that of a flat planar geometry, even though the bending stiffness of a transition portion might not be as large as that of a gripping portion. It can be noted that even though a gripping portion such as gripping portion 1100 is referred to herein as a gripping portion, it is not necessary that all of the gripping portion actually is gripped by a chuck or similar component. Typically some of the gripping portion would be gripped but it is not necessary that all of the gripping portion would be gripped. It is furthermore believed, although it is not wished to be limited to this explanation, that the gradually changing nature of a transition portion results in little or no stress concentration factor in the vicinity of the transition portion, which is a better situation than would occur with a more abrupt change of geometry between a gripping portion and a distal portion.

The cutting edge may be sharp, or in still further embodiments, it is possible that the cutting edges could be serrated. For uses that involve pushing rather than cutting, the distal-most edge may be blunt.

Features that are described on one embodiment can be ascribed to another embodiment, if physically possible. Similar although not identical part numbers are used in certain places.

The blade can have dimensional scale or markings, which can be useful for enabling the user to obtain approximate indication of depth or distance along the longitudinal direction of the blade.

The blade can have a beveled or sharp edge that, in the case of a distal portion whose cross-sectional shape is concave, may be located at the concave (i.e., inner) surface of the distal end, which for appropriate blade orientations may be thought of as the upper surface. Alternatively, the beveled or sharp edge may be located at the convex (i.e., outer) surface of the distal end, which for appropriate blade orientations may be thought of as the lower surface. As yet another alternative, the beveled or sharp edge may be located between the upper surface and the lower surface of the distal end.

The term V-shaped is meant to include either a pointed vertex or a rounded vertex. The term concave is intended to apply to a variety of shapes and meant to include not just shapes that are strictly curves, but also to include V-shapes having either pointed vertices or rounded vertices. The same is true for the term convex.

In general, the described features of gripping portion 1100 can be used in combination with any design for other portions of the blade.

If the chuck is part of a driving device or power tool such as an osteotome, the power tool may oscillate or impact blade 10 in a forward-rearward (proximal-distal) direction. This would be consistent with the illustrated blade 10 having a sharp edge on its forward (distal) edge. However, in other embodiments, it is possible that a power tool could oscillate blade 10 in a side-to-side pattern of motion. In such a situation, other edges of the cutting portion could be sharp or shaped for purposes of cutting. Of course, still other or more complex patterns of motion and blade edge configuration are also possible.

In regard to materials, blade 10 may in general be made of a metal that is suitable for use in a surgical setting. The blades can be made from any strong material or combination of materials that can withstand the impact forces of the cutting action while maintaining a sharp cutting edge. Some examples are 300 and 400 series stainless steels, carbon fiber, ceramic, nickel titanium, etc. The splash guard 9000 may be made of a polymer such as rubber. The chuck may generally be made of a suitable metal, although other materials are also possible.

In general, any combination of disclosed features, components and methods described herein, that is physically possible, is intended to be within the scope of the claims.

All cited references are incorporated by reference herein.

Although embodiments have been disclosed, it is not desired to be limited thereby. Rather, the scope should be determined only by the appended claims.

I claim:

1. A blade, said blade comprising:
a gripping portion;
a transition portion that is continuous with said gripping portion; and
a distal portion that is continuous with said transition portion,
wherein said gripping portion has a longitudinal axis and has a gripping portion cross-sectional shape taken perpendicular to said longitudinal axis,
wherein said gripping portion has a gripping portion major surface that does not entirely lie in a single plane,
wherein said distal portion has a distal portion cross-sectional shape that is different from said gripping portion cross-sectional shape,
wherein said transition portion has a three-dimensional surface transitioning between said gripping portion and said distal portion.

2. The blade of claim 1, wherein said distal portion has a distal portion major surface that is concave and has a cross-sectional shape that is curved or is V-shaped having either a sharp vertex or a rounded vertex.

3. The blade of claim 1, wherein said gripping portion cross-sectional shape is a "V" shape having either a pointed vertex or a rounded vertex, or is a curved shape.

4. The blade of claim 1, wherein said gripping portion comprises two legs each of which is generally parallel to said longitudinal direction but which are separate from each other for at least a portion of said gripping portion.

5. The blade of claim 1, wherein said gripping portion comprises at least one hole therethrough, or a shoulder feature on at least one side of said gripping portion, or both.

6. The blade of claim 1, wherein said distal portion comprises a tip made of a tip material that is different from a material of a remainder of said blade.

7. The blade of claim 1, wherein said gripping portion has a gripping portion width, and said distal portion has a distal portion width, and said gripping portion width is greater than said distal portion width.

8. The blade of claim 1, wherein said distal portion terminates in a cutting edge, and said cutting edge has a shape along said edge that is selected from the group consisting of straight, concavely curved, and convexly curved.

9. The blade of claim 1, wherein said distal portion terminates in a cutting edge, and said cutting edge is contiguous with a distal portion surface that is concave.

10. The blade of claim 1, wherein said distal portion terminates in a cutting edge, and said cutting edge is contiguous with a distal portion surface that is convex.

11. The blade of claim 1, wherein said distal portion has a cross-sectional shape that is concave, and said distal portion terminates in a cutting edge that is concave when viewed perpendicular to a plane that extends generally from one edge of said distal portion to an opposed edge of said distal portion, and said cutting edge is contiguous with a distal portion surface that is convex.

12. The blade of claim 1, further comprising a splash guard that engages with a feature of said blade.

13. The blade of claim 1, wherein said distal portion has a distal portion major surface that is concave facing a first direction and wherein said transition portion and said distal portion proceeds along a path and at least a portion of said path is concave facing said first direction.

14. The blade of claim 1, wherein said distal portion has a distal portion major surface that is concave facing a first direction and wherein said transition portion and said distal portion proceeds along a path and at least a portion of said path is concave with respect to said first direction.

15. The blade of claim 1, wherein said distal portion has a distal portion major surface that is concave facing a first direction and wherein a path proceeding distally from said gripping portion comprises a path segment that is convex with respect to said first direction, followed by a path segment that is concave with respect to said first direction.

16. The blade of claim 1, wherein said gripping portion and said transition portion and said distal portion all lie along said longitudinal direction.

17. The blade of claim 16, wherein said gripping portion has an upper extreme bounding plane parallel to said longitudinal axis and has a lower extreme bounding plane parallel to said longitudinal axis, and wherein said distal portion lies between said extreme bounding planes.

18. The blade of claim 16, wherein said gripping portion has a gripping portion height, and said distal portion has a distal portion height, and wherein said gripping portion height is greater than said distal portion height.

19. The blade of claim 16, wherein said distal portion is planar and wherein said transition portion comprises a first transitional sub-region and a mid-region and a second transitional sub-region, wherein said first transitional sub-region is continuous with said gripping portion and is continuous with said mid-region, and said second transitional sub-region is continuous with said mid-region and with said distal portion.

* * * * *